US005753492A

United States Patent [19]
Schnepf et al.

[11] Patent Number: 5,753,492
[45] Date of Patent: May 19, 1998

[54] GENES ENCODING NEMATODE-ACTIVE TOXINS FROM BACILLUS THURINGIENSIS STRAINS

[75] Inventors: H. Ernest Schnepf, San Diego; George E. Schwab, La Jolla; Jewel Payne, Davis; Kenneth E. Narva, San Diego; Luis Foncerrada, Vista, all of Calif.

[73] Assignee: Mycogen Corporation, San Diego, Calif.

[21] Appl. No.: 316,301

[22] Filed: Sep. 30, 1994

Related U.S. Application Data

[60] Division of Ser. No. 871,510, Apr. 23, 1992, abandoned, which is a continuation-in-part of Ser. No. 693,018, May 3, 1991, abandoned, which is a continuation-in-part of Ser. No. 565,544, Aug. 10, 1990, abandoned, which is a continuation-in-part of Ser. No. 84,653, Aug. 12, 1987, Pat. No. 4,948,734, which is a continuation-in-part of Ser. No. 830,050, Jan. 31, 1992, abandoned.

[51] Int. Cl.$^6$ .................................................. C12N 15/32
[52] U.S. Cl. ........................... 435/252.3; 536/23.71; 435/325; 435/419
[58] Field of Search .................. 536/23.71; 435/240.1, 435/240.2, 240.4, 252.3, 252.33, 325, 419; 530/350

[56] References Cited

U.S. PATENT DOCUMENTS

| | | | |
|---|---|---|---|
| 4,948,734 | 8/1990 | Edwards et al. | 514/2 |
| 5,281,530 | 1/1994 | Sick et al. | 435/252.3 |
| 5,426,049 | 6/1995 | Sick et al. | 435/252.3 |

OTHER PUBLICATIONS

Shin et al., *App. & Environ. Microb.*, Jun. 1995, vol. 61, No. 6, pp. 2402–2407.

Chambers et al., *J. Bact.*, vol. 173, No. 13, Jul. 1991, pp. 3966–3976.

Prichard, R.K. et al. (1980) "The Problem of Anthelmintic Resistance in Nematodes" Australian Veterinary Journal 56:239–251.

Coles, G.C. (1986) "Anthelmintic Resistance in Sheep" Veterinary Clinics of North America: Food Animal Practice 2(2):423–432.

Bottjer, K.P., L.W. Bone, S.S. Gill (1985) "Nematoda: Susceptibility of the Egg to *Bacillus thuringiensis* Toxins" Experimental Parasitology 60:239–244.

Ignoffo, C.M., V.H. Dropkin (1977) "Deleterious Effects of the Thermostable Toxin of *Bacillus thuringiensis* on Species of Soil–Inhabiting, Myceliophagus, and Plant–Parasitic Nematodes" Journal of the Kansas Entomological Society 50(3):394–398.

Ciordia, H., W.E. Bizzell (1961) "A Preliminary Report of the Effects of *Bacillus thuringiensis* var. thuringiensis Berliner on the Development of the Free–Living Stages of Some Cattle Nematodes" Journal of Parisitology 47:41, Abstract No. 86.

Hofte, H., H.R. Whiteley (1989) "Insecticidal Crystal Proteins of *Bacillus thuringiensis*" Microbiological Reviews 53(2):242–255.

Suggs, S.V. et al. (1981) "Use of synthetic oligonucleotides as hybridization probes: Isolation of cloned cDNA sequences for human $\beta_2$–microglobulin"Proc. Natl. Acad. Sci. USA 78(11):6613–6617.

Prefontaine, G. et al. (1987) "Use of Oligonucleotide Probs to Study the Relatedness of Delta–Endotoxin Genes among *Bacillus thuringiensis* Subspecies and Strains" Applied and Environmental Microbiology 53(12):2808–2814.

Haider, M.Z. et al. (1987) "Cloning and heterologous expression of an insecticidal delta–endotoxin gene from *Bacillus thuringiensis* var. aizawai IC1 toxic to both lepidoptera and diptera" Gene 52:285–290.

*Primary Examiner*—Keith D. Hendricks
*Attorney, Agent, or Firm*—Saliwanchik, Lloyd & Saliwanchik

[57] ABSTRACT

This invention concerns genes or gene fragments which have been cloned from novel *Bacillus thuringiensis* isolates which have nematicidal activity. These genes or gene fragments can be used to transform suitable hosts for controlling nematodes.

8 Claims, No Drawings

GENES ENCODING NEMATODE-ACTIVE TOXINS FROM *BACILLUS THURINGIENSIS* STRAINS

CROSS-REFERENCE TO A RELATED APPLICATION

This is a division of application Ser. No. 07/871,510, filed on Apr. 23, 1992, now abandoned; which is a continuation-in-part of application Ser. No. 07/693,018, filed on May 3, 1991, now abandoned; which is a continuation-in-part of Ser. No. 07/565,544, filed on Aug. 10, 1990, now abandoned; which is a continuation-in-part of application Ser. No. 07/084,653, filed on Aug. 12, 1987, now U.S. Pat. No. 4,948,734. This is also a continuation-in-part of application Ser. No. 07/830,050, filed on Jan. 31, 1992, now abandoned.

BACKGROUND OF THE INVENTION

Regular use of chemicals to control unwanted organisms can select for chemical resistant strains. This has occurred in many species of economically important insects and has also occurred in nematodes of sheep, goats, and horses. The development of chemical resistance necessitates a continuing search for new control agents having different modes of action.

In recent times, the accepted methodology for control of nematodes has centered around the drug benzimidazole and its congeners. The use of these drugs on a wide scale has led to many instances of resistance among nematode populations (Prichard, R. K. et al. [1980] "The problem of anthelmintic resistance in nematodes," Austr. Vet. J. 56:239–251; Coles, G. C. [1986] "Anthelmintic resistance in sheep," In *Veterinary Clinics of North America: Food Animal Practice*, Vol 2:423–432 [Herd, R. P., eds.] W. B. Saunders, New York). There are more than 100,000 described species of nematodes.

The bacterium *Bacillus thuringiensis* (*B.t.*) produces a δ-endotoxin polypeptide that has been shown to have activity against a rapidly growing number of insect species. The earlier observations of toxicity only against lepidopteran insects have been expanded with descriptions of *B.t.* isolates with toxicity to dipteran and coleopteran insects. These toxins are deposited as crystalline inclusions within the organism. Many strains of *B.t.* produce crystalline inclusions with no demonstrated toxicity to any insect tested.

A small number of research articles have been published about the effects of delta endotoxins from *B. thuringiensis* species on the viability of nematode eggs. Bottjer, Bone and Gill (Experimental Parasitology 60:239–244, 1985) have reported that *B.t. kurstaki* and *B.t. israelensis* were toxic in vitro to eggs of the nematode *Trichostrongylus colubfifonmis*. In addition, 28 other *B.t.* strains were tested with widely variable toxicities. The most potent had $LD_{50}$ values in the nanogram range. Ignoffo and Dropkin (Ignoffo, C. M. and Dropkin, V. H. [1977] J. Kans. Entomol. Soc. 50:394–398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuningiensis* on some cattle nematodes.

At the present time there is a need to have more effective means to control the many nematodes that cause considerable damage to susceptible hosts. Advantageously, such effective means would employ biological agents.

BRIEF SUMMARY OF THE INVENTION

The subject invention concerns novel toxins active against nematodes. A further aspect of the invention concerns genes coding for nematicidal toxins. The subject invention provides the person skilled in this art with a vast array of nematicidal toxins, methods for using these toxins, and genes that code for the toxins.

One aspect of the invention is the discovery of two generalized chemical formulae common to a wide range of nematicidal toxins. These formulae can be used by those skilled in this art to obtain and identify a wide variety of toxins having the desired nematicidal activity. The subject invention concerns other teachings which enable the skilled practitioner to identify and isolate nematode active toxins and the genes which code therefor. For example, characteristic features of nematode-active toxin crystals are disclosed herein. Furthermore, characteristic levels of amino acid homology can be used to characterize the toxins of the subject invention. Yet another characterizing feature pertains to immunoreactivity with certain antibodies. Also, nucleotide probes specific for genes encoding toxins with nematicidal activity are described.

In addition to the teachings of the subject invention which define groups of *B.t.* toxins with advantageous nematicidal activity, a further aspect of the subject invention is the provision of specific nematicidal toxins and the nucleotide sequences which code for these toxins.

One aspect of the of the subject invention is the discovery of two groups of *B.t.*-derived nematode-active toxins. One group (CryV) is exemplified by the gene expression products of PS17, PS33F2 and PS63B, while the other group (CryVI) is exemplified by the gene expression products of PS52A1 and PS69D1. The organization of the toxins within each of the two groups can be accomplished by sequence-specific motifs, overall sequence similarity, immunoreactivity, and ability to hybridize with specific probes.

The genes or gene fragments of the invention encode *Bacillus thuringiensis* δ-endotoxins which have nematicidal activity. The genes or gene fragments can be transferred to suitable hosts via a recombinant DNA vector.

BRIEF DESCRIPTION OF THE SEQUENCES

SEQ ID NO. 1 discloses the DNA of 17a.

SEQ ID NO. 2 discloses the amino acid sequence of the toxin encoded by 17a.

SEQ ID NO. 3 discloses the DNA of 17b.

SEQ ID NO. 4 discloses the amino acid sequence of the toxin encoded by 17b.

SEQ ID NO. 5 is the nucleotide sequence of a gene from 33F2.

SEQ ID NO. 6 is the amino acid sequence of the protein expressed by the gene from 33F2.

SEQ ID NO. 7 is the nucleotide sequence of a gene from 52A1.

SEQ ID NO. 8 is the amino acid sequence of the protein expressed by the gene from 52A1.

SEQ ID NO. 9 is the nucleotide sequence of a gene from 69D1.

SEQ ID NO. 10 is the amino acid sequence of the protein expressed by the gene from 69D1.

SEQ ID NO. 11 is the nucleotide sequence of a gene from 63B.

SEQ ID NO. 12 is the amino acid sequence of the protein expressed by the gene from 63B.

SEQ ID NO. 13 is the amino acid sequence of a probe which can be used according to the subject invention.

SEQ ID NO. 14 is the DNA coding for the amino acid sequence of SEQ ID NO. 13.

SEQ ID NO. 15 is the amino acid sequence of a probe which can be used according to the subject invention.

SEQ ID NO. 16 is the DNA coding for the amino acid sequence of SEQ ID NO. 15.

SEQ ID NO. 17 is the N-terminal amino acid sequence of 17a.

SEQ ID NO. 18 is the N-terminal amino acid sequence of 17b.

SEQ ID NO. 19 is the N-terminal amino acid sequence of 52A1.

SEQ ID NO. 20 is the N-terminal amino acid sequence of 63B.

SEQ ID NO. 21 is the N-terminal amino acid sequence of 69D1.

SEQ ID NO. 22 is the N-terminal amino acid sequence of 33F2.

SEQ ID NO. 23 is an internal amino acid sequence for 63B.

SEQ ID NO. 24 is a synthetic oligonucleotide derived from 17.

SEQ ID NO. 25 is an oligonucleotide probe designed from the N-terminal amino acid sequence of 52A1.

SEQ ID NO. 26 is the synthetic oligonucleotide probe designated as 69D1-D.

SEQ ID NO. 27 is the forward oligonucleotide primer from 63B.

SEQ ID NO. 28 is the reverse oligonucleotide primer from 63B.

SEQ ID NO. 29 is the nematode (NEMI) variant of region 5 of Hofte and Whiteley.

SEQ ID NO. 30 is the reverse complement primer to SEQ ID NO. 29, used according to the subject invention.

SEQ ID NO. 31 is a reverse oligonucleotide primer used according to the subject invention.

SEQ ID NO. 32 is the DNA coding for the primer of SEQ ID NO. 31.

SEQ ID NO. 33 is oligonucleotide probe 33F2A.

SEQ ID NO. 34 is oligonucleotide probe 33F2B.

SEQ ID NO. 35 is a reverse primer used according to the subject invention.

SEQ ID NO. 36 is a forward primer according to the subject invention.

SEQ ID NO. 37 is a probe according to the subject invention.

SEQ ID NO. 38 is a probe according to the subject invention.

SEQ ID NO. 39 is a probe according to the subject invention.

SEQ ID NO. 40 is a forward primer according to the subject invention.

SEQ ID NO. 42 is an IUPAC amino acid sequence representation of the Generic Formula I according to the subject invention.

SEQ ID NO. 42 is an IUPAC amino acid sequence representation of the Generic Formula II according to the subject invention.

DETAILED DISCLOSURE OF THE INVENTION

The subject invention concerns a vast array of B.t. δ-endotoxins having nematicidal activity. In addition to having nematicidal activity, the toxins of the subject invention will have one or more of the following characteristics:

1. An amino acid sequence according to either of the two generic formulae disclosed herein.
2. A high degree of amino acid homology with specific toxins disclosed herein.
3. A DNA sequence encoding the toxin which hybridizes with probes or genes disclosed herein.
4. A nucleotide sequence which can be amplified using primers disclosed herein.
5. A crystal toxin presentation as described herein.
6. Immunoreactivity to an antibody raised to a specific toxin disclosed herein.

One aspect of the subject invention concerns the discovery of generic chemical formulae which describe toxins having activity against nematodes. Two formulae are provided: one which pertains to nematicidal toxins having molecular weights of between about 45 kDa and 65 kDa, and the other pertains to larger nematicidal proteins having molecular weights from about 65 kDa to about 155 kDa. These formulae represent two different categories of B.t. δ-endotoxins, each of which has activity against nematodes. The formula describing smaller proteins describes many CryVI proteins, while the formula describing larger proteins describes many CryV proteins. A description of these two formulae is as follows:

Generic Formula I(SEQ ID NO. 41). This formula describes toxin proteins having molecular weights from about 65 kDa to about 155 kDa. The first 650–700 amino acids for proteins in excess of about 75 kDa and the entire molecule (for proteins of less than about 75 kDa) have substantially the following sequence:

| 1 | MOXXXXXXPX | BPYNBLOXXP | XZXXXXXXXX | OXxXXBXXXE | UXBKXBJJXX |
|---|---|---|---|---|---|
|  | XOxxxZXXZ | xXOBXJXBJX | XBXXXXBXYX | XXVUXZLZLB | xxxXXOBPXB |
| 101 | ZBXXPBLZBB | BXXBXXXXOx | xxXUXOXLBX | XBOXXBUJBL | DJXLXXXXXX |
|  | XLUXELXXBX | XLXXKXXXXB | XExxBXXHXX | BXXBXXZXXX | KBXXXXBZXX |
| 201 | ZBXOXXBXXB | LOEXXXJxxx | LXBPXYXBXO | XMXLXXXXXX | LXXZXOWXXK |
|  | BxxxxxxxX | XXXXO LXXXK | XXBKXXLXBY | XXXXXXBBXX | XLXZXZxxZX |
| 301 | XXXBXJXXXY | XJXMXXX*LE | BXXXXPOBXP | EXYxxxZZXL | XLXKOKXLBZ |
|  | XBBXXXXXxx | XZBOLXUXXX | XOXXXXXXXX | ZXXXBXXXXJ | JBXKxUBKBY |
| 401 | XXXXXXX*XX | *Bx*YXXXBX | BUXXXXOXXY | ZXxxxXEPXX | ZXXxxxBXXX |
|  | XPBXXBUXXO | XXOXXXXXXX | XXOXXXKZXB | *XLxxxxxx | *BXXKX*XXX |

-continued

| | | | | | |
|---|---|---|---|---|---|
| 501 | ZXZXZXZ*XX | XLXZXXXXXX | XXXXXXXXXXX | XZXXXxxxxx | XLBXXXXPXE |
| | XXXXUX LZXX | EXXZxUBXXX | ZBPBEKxxOZ | XXXXBxxBKE | WLUZOXXXXL |
| 601 | ZPZUZXZBXB | OUXOZZXYXB | RCRYOZXXXO | XBBBUxBXXZ | ZXUPLXXUBX |
| | BXXOXEXXOX | XXXXUXBXXB | KZLXXXXXXB | xxxxXxJLPX | XXBXBXBOUX |
| 701 | ZSSXBXLDKL | EBBPBX | | | |

Numbering is for convenience and approximate location only.

Symbols used:
A=ala
C=cys
D=asp
E=glu
F=phe
G=gly
H=his
I=ile
K=lys
L=leu
M=met
N=asn
P=pro
Q=gln
R=arg
S=ser
T=thr
V=val
W=trp
Y=tyr
K=K or R
E=E or D
L=L or I
B=M, L, I, V, or F
J=K, R, E, or D
O=A or T
U=N or Q
Z=G or S
X=any naturally occurring amino acid, except C.
*=any naturally occurring amino acid.
x=any naturally occurring amino acid, except C (or complete omission of any amino acids).

Where a stretch of wild-card amino acids are encountered (X(n) or x(n) where n>2), repetition of a given amino acid should be avoided. Similarly, P, C, E, D, K, or R utilization should be minimized.

This formula (hereinafter referred to as Generic Formula I) (SEQ ID NO. 41) is exemplified in the current application by the specific toxins 17a, 17b and 63b.

Generic Formula II (SEQ ID NO. 42). This formula describes toxin proteins having molecular weights from about 45 kDa to about 65 kDa. Their primary amino acid structure substantially follows the motif illustrated below:

The symbols used for this formula are the same as those used for Generic Formula I.

This formula (hereinafter referred to as Generic Formula II)(SEQ ID NO. 42) is exemplified in the current application by specific toxins 52A1 and 69D1.

Nematode-active toxins according to the formulae of the subject invention are specifically exemplified herein by the toxins encoded by the genes designated 17a, 17b, 63B, 52A1, and 69D1. Since these toxins are merely exemplary of the toxins represented by the generic formulae presented herein, it should be readily apparent that the subject invention further comprises equivalent toxins (and nucleotide sequences coding for equivalent toxins) having the same or similar biological activity of the specific toxins disclosed or claimed herein. These equivalent toxins will have amino acid homology with the toxins disclosed and claimed herein. This amino acid homology will typically be greater than 50%, preferably be greater than 75%, and most preferably be greater than 90%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin. The information presented in the generic formulae of

| | | | | | |
|---|---|---|---|---|---|
| 1 | MLBXXXXOBP | KHxxxXXXXO | XXXXZXKKxx | xXZPXXBXXX | XXBLLZKXEW |
| | OXBXOYBXOZ | XZLPBUJXXB | KXHBXLXXJL | XLPXJBXULY | JBYXXJKXXX |
| 101 | XWWUXXLXPL | BBKXOUJLXX | YZBKXOZJXX | KKxxZXXJXB | UJJBJULXJU |
| | XXJJOXXXKO | XKJBXOKCXL | LLKEOJUYJX | OOJXBXXXLX | XBLXZXUxxx |
| 201 | xXJBXZBXXB | UXXLXXBXXX | LXXXXZJXZP | XXJELLJKBJ | XLKXXLEXXL |
| | KOEUJLEKKB | BXZBXLZPLL | ZBBBYELLEX | OOBXXLXXXB | JXLXXXLJXO |
| 301 | UXJLJKJBKL | LZBBUZLXOJ | LJXBXXUZXX | OLXBBXKLXZ | LWXXLXXULX |
| | ULKXOZXXEB | XJXXJXJXLX | LELXJOXXXW | XXBOXEOXXB | XLUZYXXxxx |
| 401 | (x)n* | | | | |

*Where n = 0–100 the subject invention provides clear guidance to the person skilled in this art in making various amino acid substitutions.

Further guidance for characterizing the nematicidal toxins of the subject invention is provided in Tables 3 and 4, which demonstrate the relatedness among toxins within each of the above-noted groups of nematicidal toxins (CryV and CryVI). These tables show a numeric score for the best matching alignment between two proteins that reflects: (1) positive scores for exact matches, (2) positive or negative scores reflecting the likelihood (or not) of one amino acid substituting for another in a related protein, and (3) negative scores for the introduction of gaps. A protein sequence aligned to itself will have the highest possible score—i.e., all exact matches and no gaps. However, an unrelated protein or a randomly generated sequence will typically have a low positive score. Related sequences have scores between the random background score and the perfect match score.

The sequence comparisons were made using the algorithm of Smith and Waterman ([1981] Advances in Applied Mathematics 2:482–489), implemented as the program "Bestfit" in the GCG Sequence Analysis Software Package Version 7 April 1991. The sequences were compared with default parameter values (comparison table: Swgappep.Cmp, Gap weight:3.0, Length weight:0.1) except that gap limits of 175 residues were applied to each sequence compared. The program output value compared is referred to as the Quality score.

Tables 3 and 4 show the pairwise alignments between the indicated amino acids of the two classes of nematode-active proteins CryV and CryVI and representatives of dipteran (CryIV; Sen, K. et al. [1988] Agric. Biol. Chem. 52:873–878), lepidopteran and dipteran (CryIIA; Widner and Whiteley [1989] J. Bacteriol. 171:965–974), lepidopteran (CryIA(c); Adang et al. [1981] Gene 36:289–300), and coleopteran (CryhIIIA; Herrnstadt et al. [1987] Gene 57:37–46) proteins.

Table 2 shows which amino acids were compared from the proteins of interest.

TABLE 2

| Protein | Amino acids compared |
|---|---|
| 63B | 1-692 |
| 33F2 | 1-618 |
| 17a | 1-677 |
| 17b | 1-678 |
| CryIV | 1-633 |

TABLE 2-continued

| Protein | Amino acids compared |
|---|---|
| CryIIA | 1-633 |
| CryIA(c) | 1-609 |
| CryIIIA | 1-644 |
| 69D1 | 1-395 |
| 52A1 | 1-475 |

Table 3 shows the scores prior to adjustment for random sequence scores.

TABLE 3

|  | 63B | 33F2 | 17a | CryIVA | CryIIA | CryIA(c) | CryIIIA | 52A1 | 69D1 |
|---|---|---|---|---|---|---|---|---|---|
| 63B | 1038 | 274 | 338 | 235 | 228 | 232 | 244 | 154 | 122 |
| 33F2 |  | 927 | 322 | 251 | 232 | 251 | 270 | 157 | 130 |
| 17a |  |  | 1016 | 240 | 240 | 237 | 249 | 152 | 127 |
| CryIVA |  |  |  | 950 | 245 | 325 | 326 | 158 | 125 |
| CryIIA |  |  |  |  | 950 | 244 | 241 | 151 | 132 |
| CryIA(c) |  |  |  |  |  | 914 | 367 | 151 | 127 |
| CryIIIA |  |  |  |  |  |  | 966 | 150 | 123 |
| 52A1 |  |  |  |  |  |  |  | 713 | 350 |
| 69D1 |  |  |  |  |  |  |  |  | 593 |

Note that for each nematode-active protein, the highest score is always with another nematode-active protein. For example, 63B's highest score, aside from itself, is with 17a. Furthermore, 33F2's highest score, aside from itself, is also with 17a.

Similarly, 52A1 and 69D1 have a higher score versus each other than with the other proteins.

Table 4 shows the same analysis after subtraction of the average score of 50 alignments of random shuffles of the column sequences with the row sequences.

TABLE 4

|          | 63B | 33F2 | 17a | CryIVA | CryIIA | CryIA(c) | CryIIIA | 52A1 | 69D1 |
|----------|-----|------|-----|--------|--------|----------|---------|------|------|
| 63B      | 830 | 81   | 130 | 40     | 32     | 42       | 48      | 0.1  | -8.8 |
| 33F2     |     | 740  | 128 | 66     | 48     | 72       | 85      | 1.4  | -2.9 |
| 17a      |     |      | 808 | 45     | 45     | 45       | 54      | -0.8 | -5.2 |
| CryIVA   |     |      |     | 759    | 54     | 142      | 138     | 5.4  | -4.1 |
| CryIIA   |     |      |     |        | 755    | 58       | 53      | -2.3 | 6    |
| CryIA(c) |     |      |     |        |        | 728      | 185     | 3.1  | 0    |
| CryIIIA  |     |      |     |        |        |          | 766     | -2.3 | -6.9 |
| 52A1     |     |      |     |        |        |          |         | 566  | 221  |
| 69D1     |     |      |     |        |        |          |         |      | 465  |

Note that in Table 4 the same relationships hold as in Table 3, i.e., 63B's highest score, aside from itself, is with 17a, and 33F2's highest score, aside from itself, is also with 17a.

Similarly, 52A1 and 69D1 have a better score versus each other than with the other proteins.

Thus, certain toxins according to the subject invention can be defined as those which have nematode activity and either have an alignment value (according to the procedures of Table 4) greater than 100 with 17a or have an alignment value greater than 100 with 52A1. As used herein, the term "alignment value" refers to the scores obtained above and used to create the scores reported in Table 4.

The toxins of the subject invention can also be characterized in terms of the shape and location of crystal toxin inclusions. Specifically, nematode-active inclusions typically remain attached to the spore after cell lysis. These inclusions are not inside the exosporium, as in previous descriptions of attached inclusions, but are held within the spore by another mechanism. Inclusions of the nematode-active isolates are typically amorphic, generally long and/or multiple. These inclusions are distinguishable from the larger round/amorphic inclusions that remain attached to the spore. No B.t. strains that fit this description have been found to have activity against the conventional targets— Lepidoptera, Diptera, or Colorado Potato Beetle. AR nematode-active strains fit this description except one. Thus, there is a very high correlation between this crystal structure and nematode activity.

The genes and toxins according to the subject invention include not only the full length sequences disclosed herein but also fragments of these sequences, or fusion proteins, which retain the characteristic nematicidal activity of the sequences specifically exemplified herein.

It should be apparent to a person skilled in this art that genes coding for nematode-active toxins can be identified and obtained through several means. The specific genes may be obtained from a culture depository as described below. These genes, or portions thereof, may be constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be located from B.t. isolates and/or DNA libraries using the teachings provided herein. There are a number of methods for obtaining the nematode-active toxins of the instant invention which occur in nature. For example, antibodies to the nematode-active toxins disclosed and claimed herein can be used to identify and isolate other toxins from a mixture of proteins. Specifically, antibodies may be raised to the portions of the nematode-active toxins which are most constant and most distinct from other B.t. toxins. These antibodies can then be used to specifically identify equivalent toxins with the characteristic nematicidal activity by immunoprecipitation, enzyme linked immunoassay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying nematicidal endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed test sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

Specific nucleotide probes useful, according to the subject invention, in the rapid identification of nematode-active genes are (i) DNA coding for a peptide sequence whose single letter amino acid designation is "REWINGAN" (SEQ ID NO. 13) or variations thereof which embody point mutations according to the following: position 1, R or P or K; position 3, W or Y; position 4,I or L; position 8, N or P; a specific example of such a probe is "AGA(A or G)T(G or A)(G or T)(A or T)T(A or T)AATGG(A or T)GC(G or T)(A or C)A(A or T)" (SEQ ID NO. 14);

(ii) DNA coding for a peptide sequence whose single letter amino acid designation is "PTFDPDLY" (SEQ ID NO. 15) or variations thereof which embody point mutations according to the following: position 3, F or L; position 4, D or Y; position 7, L or H or D; a specific example of such a probe is "CC(A or T)AC(C or T)TTT(T or G)ATCCAGAT(C or G)(T or A)(T or C)TAT" (SEQ ID NO. 16).

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the B.t. toxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

The toxin genes or gene fragments exemplified according to the subject invention can be obtained from nematode-active B. thuringiensis (B.t.) isolates designated PS17, PS33F2, PS63B, PS52A1, and PS69D1. Subcultures of the E. coli host harboring the toxin genes of the invention were deposited in the permanent collection of the Northern Research Laboratory, U.S. Department of Agriculture, Peoria, Ill., USA. The accession numbers are as follows:

| Culture | Repository No. | Deposit Date |
| --- | --- | --- |
| B.t. isolate PS17 | NRRL B-18243 | July 28, 1987 |
| B.t. isolate PS33F2 | NRRL B-18244 | July 28, 1987 |
| B.t. isolate PS63B | NRRL B-18246 | July 28, 1987 |
| B.t. isolate PS52A1 | NRRL B-18245 | July 28, 1987 |
| B.t. isolate PS69D1 | NRRL B-18247 | July 28, 1987 |
| E. coli NM522(pMYC 2316) | NRRL B-18785 | March 15, 1991 |
| E. coli NM522(pMYC 2321) | NRRL B-18770 | February 14, 1991 |
| E. coli NM522(pMYC 2317) | NRRL B-18816 | April 24, 1991 |
| E. coli NM522(pMYC 1627) | NRRL B-18651 | May 11, 1990 |
| E. coli NM522(pMYC 1628) | NRRL B-18652 | May 11, 1990 |
| E. coli NM522(pMYC 1642) | NRRL B-18961 | April 10, 1992 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The novel *B.t.* genes or gene fragments of the invention encode toxins which show activity against tested nematodes. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes wide-spread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Tfhchonema, Dictyocaulus, Capillaria, Heterakis, Toxocara, Ascaridia, Oxyuris, Ancylostoma, Uncinaria, Toxascaris, Caenorhabditis and Parascaris. Certain of these, such as Nematodirus, Cooperia, and Oesophagostomum, attack primarily the intestinal tract, while others, such as Dictyocaulus are found in the lungs. Still other parasites may be located in other tissues and organs of the body.

The toxins encoded by the novel *B.t.* genes of the invention are useful as nematicides for the control of soil nematodes and plant parasites selected from the genera Bursaphalenchus, Criconemella, Diiylenchus, Globodera, Helicotylenchus, Heterodera, Melodoigyne, Pratylenchus, Radolpholus, Rotelynchus, or Tylenchus.

Alternatively, because some plant parasitic nematodes are obligate parasites, genes coding for nematicidal *B.t.* toxins can be engineered into plant cells to yield nematode-resistant plants. The methodology for engineering plant cells is well established (cf. Nester, E. W., Gordon, M. P., Amasino, R. M. and Yanofsky, M. F., Ann. Rev. Plant Physiol. 35:387–399, 1984).

The *B.t.* toxins of the invention can be administered orally in a unit dosage form such as a capsule, bolus or tablet, or as a liquid drench when used as an anthelmintic in mammals, and in the soil to control plant nematodes. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiparasitic compounds may be administered to animals parenterally, for example, by intraruminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed oil and the like. Other parenteral vehicles, such as organic preparations using solketal, glycerol, formal and aqueous parenteral formulations, are also used. The active compound compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

The toxin genes or gene fragments of the subject invention can be introduced into a wide variety of microbial hosts. Expression of the toxin gene results, directly or indirectly, in the intracellular production and maintenance of the nematicide. With suitable hosts, e.g., Pseudomonas, the microbes can be applied to the situs of nematodes where they will proliferate and be ingested by the nematodes. The result is a control of the nematodes. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene or gene fragment is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the nematicide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes;

fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti Alcaligenes entrophus,* and *Azotobacter vinlandii*; and phytosphere yeast species such as *Rhodotorula rubra, R glutinis, R marina, R aurantiaca, Cryptococcus albidus, C diffluens, C laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are known and available for introducing the *B.t.* genes or gene fragments expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for nematicidal activity.

Suitable host cells, where the nematicide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Eschenichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene or gene fragment into the host, availability of expression systems, efficiency of expression, stability of the nematicide in the host, and the presence of auxiliary genetic capabilities. Characteristics of interest for use as a nematicide microcapsule include protective qualities for the nematicide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula sp., Aureobasidium sp., Saccharomyces sp.,* and *Sporobolomyces sp.*; phylloplane organisms such as *Pseudomonas sp., Erwinia sp.* and *Flavobacterium sp.*; or such other organisms as *Escherichia, Lactobacillus sp., Bacillus sp.,* and the like. Specific organisms include *Pseudomonas aeruginosa, Pseudomonas fluorescens, Saccharomyces cerevisiae, Bacillus thutingiensis, Eschenchia coli Bacillus subtilis,* and the like.

The cell will usually be intact and be substantially in the proliferative form when treated, rather than in a spore form, although in some instances spores may be employed.

Treatment of the microbial cell, e.g., a microbe containing the *B.t.* toxin gene or gene fragment, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* nematicidal gene or gene fragment may be grown in any convenient nutrient medium, where the DNA construct provides a selective advantage, providing for a selective medium so that substantially all or all of the cells retain the *B.t.* gene or gene fragment. These cells may then be harvested in accordance with conventional ways. Alternatively, the cells can be treated prior to harvesting.

The various methods employed in the preparation of the plasmids and transformation of host organisms are well known in the art. These procedures are all described in Maniatis, T., Fritsch, E. F., and Sambrook, J. (1982) *Molecular Cloning. A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The *B.t.* cells may be formulated in a variety of ways. They may be employed as wettable powders, granules or dusts, by mixng with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The nematicide concentration will vary widely depending upon the nature of the particular formulation, particularly whether it is a concentrate or to be used directly. The nematicide will be present in at least 1% by weight and may be 100% by weight. The dry formulations will have from about 1–95% by weight of the nematicide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the nematodes, e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolates of the Invention

A subculture of a B.t. isolate can be used to inoculate the following medium, a peptone, glucose, salts medium.

| Bacto Peptone | 7.5 g/l |
| --- | --- |
| Glucose | 1.0 g/l |
| $KH_2PO_4$ | 3.4 g/l |
| $K_2HPO_4$ | 4.35 g/l |
| Salts Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

EXAMPLE 2

Purification of Protein and Amino Acid Sequencing

The B.t. isolates PS17, PS63B, PS52A1, and PS69D1 were cultured as described in Example 1. The parasporal inclusion bodies were partially purified by sodium bromide (28–38%) isopycnic gradient centrifugation (Pfannenstiel, M. A., E. J. Ross, V. C. Kramer, and K. W. Nickerson [1984] FEMS Microbiol. Lett. 21:39). The proteins toxic for the nematode Caenorhabditis elegans were bound to PVDF membranes (Millipore, Bedford, Mass.) by western blotting techniques (Towbin, H., T. Staehlelin, and K. Gordon [1979] Proc. Natl. Acad. Sci. USA 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] Meth. Enzymol. 91:399). The sequences obtained were:

PS17a: AILNELYPSVPYNV(SEQ ID NO. 17)
PS17b: AILNELYPSVPYNV(SEQ ID NO. 18)
PS52A1: MIIDSKTTLPRHSLINT(SEQ ID NO. 19)
PS63B: QLQAQPLIPYNVLA(SEQ ID NO. 20)
PS69D1: MILGNGKTLPKHIRLAHIFATQNS(SEQ ID NO. 21)
PS33F2: A T L N E V Y P V N (SEQ ID NO. 22)

In addition, internal amino acid sequence data were derived for PS63B. The toxin protein was partially digested with Staphylococcus aureus V8 protease (Sigma Chem. Co., St. Louis, Mo.) essentially as described (Cleveland, D. W., S. G. Fischer, M. W. Kirschner, and U. K. Laemmli [1977] J. Biol. Chem. 252:1102). The digested material was blotted onto PVDF membrane and a ca. 28 kDa limit peptide was selected for N-terminal sequencing as described above. The sequence obtained was:

PS63B(2) VQRILDEKLSFQLIK(SEQ ID NO.23)

From these sequence data oligonucleotide probes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from nematicidal B.t. isolates. RFLP analysis of restricted total cellular DNA using radiolabeled oligonucleotide probes has elucidated different genes or gene fragments.

EXAMPLE 3

Cloning of Novel Toxin Genes and Transformation into Escherichia coli

Total cellular DNA was prepared by growing the cells B.t. PS17 to a low optical density ($OD_{600}$=1.0) and recovering the cells by centrifugation. The cells were protoplasted in TES buffer (30 mM Tris-Cl, 10 mM EDTA, 50 mM NaCl, pH =8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50 mM Tris-HCl, 20 mM NaOAc, 2.5 mM EDTA, pH=8.0) buffered gel. A Southern blot of the gel was hybridized with a [$^{32}$P]—radiolabeled oligonucleotide probe derived from the N-terminal amino acid sequence of purified 130 kDa protein from PS17. The sequence of the oligonucleotide synthesized is (GCAATTTTAAATGAATTATATCC) (SEQ ID NO. 24). Results showed that the hybridizing EcoRI fragments of PS17 are 5.0 kb, 4.5 kb, 2.7 kb and 1.8 kb in size, presumptively identifying at least four new nematode-active toxin genes, PS17d, PS17b, PS17a and PS17e, respectively.

A library was constructed from PS17 total cellular DNA partially digested with Sau3A and size fractionated by electrophoresis. The 9 to 23 kb region of the gel was excised and the DNA was electroeluted and then concentrated using an Elutip™m ion exchange column (Schleicher and Schuel, Keene N.H.). The isolated Sau3A fragments were ligated into LambdaGEM-11™ (PROMEGA). The packaged phage were plated on KW251 *E. coli* cells (PROMEGA) at a high titer and screened using the above radiolabeled synthetic oligonucleotide as a nucleic acid hybridization probe. Hybridizing plaques were purified and rescreened at a lower plaque density. Single isolated purified plaques that hybridized with the probe were used to infect KW251 *E. coli* cells in liquid culture for preparation of phage for DNA isolation. DNA was isolated by standard procedures.

Recovered recombinant phage DNA was digested with EcoRI and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5 kb (PS17b) or the 2.7 kb (PS17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pBClac, an *E. coli/B.t.* shuttle vector comprised of replication origins from pBC16 and pUC19. The ligation mix was introduced by transformation into NM522 competent *E. coli* cells and plated on LB agar containing ampicillin, isopropyl-(Beta)-D-thiogalactoside (IPTG)and5-Bromo-4-Chloro-3-indolyl-(Beta)-D-galactoside (XGAL). White colonies, with putative insertions in the (Beta)-galactosidase gene of pBClac, were subjected to standard rapid plasmid purification procedures to isolate the desired plasmids. The selected plasmid containing the 2.7 kb EcoRI fragment was named pMYC1627 and the plasmid containing the 4.5 kb EcoRI fragment was called pMYC1628.

The toxin genes were sequenced by the standard Sanger dideoxy chain termination method using the synthetic oligonucleotide probe, disclosed above, and by "walking" with primers made to the sequence of the new toxin genes.

The PS17 toxin genes were subcloned into the shuttle vector pHT3101 (Lereclus, D. et al. [1989] FEMS Microbiol. Lett. 60:211–218) using standard methods for expression in *B.t.* Briefly, SalI fragments containing the 17a and 17b toxin genes were isolated from pMYC1629 and pMYC1627, respectively, by preparative agarose gel electrophoresis, electroelution, and concentrated, as described above. These concentrated fragments were ligated into SalI-cleaved and dephosphorylated pHT3101. The ligation mixtures were used separately to transform frozen, competent *E. coli* NM522. Plasmids from each respective recombinant *E. coli* strain were prepared by alkaline lysis and analyzed by agarose gel electrophoresis. The resulting subclones, pMYC2311 and pMYC2309, harbored the 17a and 17b toxin genes, respectively. These plasmids were transformed into the acrystalliferous *B.t.* strain, HD-1 cryB (Aronson, A., Purdue University, West Lafayette, Ind.), by standard electroporation techniques (Instruction Manual, Biorad, Richmond, Calif.).

Recombinant *B.t.* strains HD-1 cryB [pMYC2311] and [pMYC2309] were grown to sporulation and the proteins purified by NaBr gradient centrifugation as described above for the wild-type *B.t.* proteins.

EXAMPLE 4

Activity of the *B.t.* Toxin Protein and Gene Product Against *Caenorhabditis elegans*

Caenorhabditis elegans (CE) was cultured as described by Simpkin and Coles (J. Chem. Tech. Biotechnol. 31:66–69, 1981) in corning (Corning Glass Works, Corning, N.Y.) 24-well tissue culture plates containing 1 ml S-basal media, 0.5 mg ampicillin and 0.01 mg cholesterol. Each well also contained ca. $10^8$ cells of *Escherichia coli* strain OP-50, a uracil auxotroph. The wells were seeded with ca. 100–200 CE per well and incubated at 20° C. Samples of protein (obtained from the wild type *B.t.* or the recombinant *B.t.*) were added to the wells by serial dilution. Water served as the control as well as the vehicle to introduce the proteins to the wells.

Each of the wells were examined daily and representative results are as follows:

| | % Kill with protein from indicated isolate | | |
|---|---|---|---|
| µg Toxin | HD-1 cryB [pMYC2309] | HD-1 cryB [pMYC 2311] | PS17 |
| 100 | 25 | 50 | 75 |
| 32 | 25 | 50 | 75 |
| 10 | 50 | 25 | 50 |
| 1 | 0 | 0 | 0 |

EXAMPLE 5

Molecular Cloning of Gene Encoding a Novel Toxin From *Bacillus thuringiensis* strain PS52A1

Total cellular DNA was prepared from *Bacillus thuringiensis* PS52A1 (*B.t.* PS52A1) as disclosed in Example 3.

RFLP analyses were performed by standard hybridization of Southern blots of PS52A1 DNA with a $^{32}$P-labeled oligonucleotide probe designed from the N-terminal amino acid sequence disclosed in Example 2. The sequence of this probe is:

5' ATG ATT ATT GAT TCT AAA ACA ACA TTA CCA AGA CAT TCA TT TTA ATA/T AAT ACA[T ATA/T AA 3' (SEQ ID NO. 25)

This probe was designated 52A1-C. Hybridizing bands included an approximately 3.6 kbp HindIII fragment and an approximately 8.6 kbp EcoRV fragment. A gene library was constructed from PS52A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega). Recombinant phage were packaged and plated on *E. coli* KW251 cells (Promega). Plaques were screened by hybridization with the radiolabeled 52A1-C oligonucleotide probe disclosed above. Hybridizing phage were plaque-purified and used to infect liquid cultures of *E. coli* KW251 cells for isolation of phage DNA by standard procedures (Maniatis et al.). For subcloning, preparative amounts of DNA were digested with EcoRI and SalI, and electrophoresed on an agarose gel. The approximately 3.1 kbp band containing the toxin gene was excised from the gel, electroeluted from the gel slice, and purified by ion exchange chromatography as above. The purified DNA insert was ligated into EcoRI+ SalI-digested pHTBlueII (an *E. coli/B. Thuringiensis* shuttle vector comprised of pBluescript S/K [Stratagene] and the replication origin from a resident *B.t.* plasmid [D. Lereclus et a]. 1989. FEMS Microbiology Letters 60:211–218]). The ligation mix was used to transform frozen, competent *E. coli* NM522 cells (ATCC 47000). Transformants were plated on LB agar containing ampicillin, isopropyl-(Beta)-D-thiogalactoside (IPTG), and 5-Bromo-4-Chloro-3-indolyl-(Beta)-D-galactoside (XGAL). Plasmids were purified from putative recombinants by alkaline lysis (Maniatis et al.) and analyzed by electrophoresis of EcoRI and SalI digests on agarose gels. The desired plasmid construct, pMYC2321 contains a toxin gene that is novel compared to the maps of other toxin genes encoding nematicidal proteins.

Plasmid pMYC2321 was introduced into an acrystalliferous (Cry−) B.t. host by electroporation. Expression of an approximately 55–60 kDa crystal protein was verified by SDS-PAGE analysis. NaBr-purified crystals were prepared as described in Example 3 for determination of toxicity of the cloned gene product to Pratylenchus spp.

EXAMPLE 6

Activity of the B.t. PS52A1 Toxin Protein and Gene Product Against the Root Lesion Nematode, Pratylenchus scribneri Pratylenchus scribneri was reared aseptically on excised corn roots in Gamborg's B5 medium (GIBCO Laboratories, Grand Island, N.Y.). Bioassays were done in 24 well assay plates (Corning #25820) using L 3–4 larvae as described by Tsai and Van Gundy (J. Nematol. 22(3):327–332). Approximately 20 nematodes were placed in each well. A total of 80–160 nematodes were used in each treatment. Samples of protein were suspended in aqueous solution using a hand-held homogenizer.

Mortality was assessed by prodding with a dull probe 7 days after treatment. Larvae that did not respond to prodding were considered moribund. Representative results are shown below.

| Rate (ppm) | Percent Moribund |
| --- | --- |
| 200 | 75 |
| Control | 5 |

EXAMPLE 7

Molecular Clonings of Gene Encoding a Novel Toxin From Bacillus Thuringensis strain PS69D1

Total cellular DNA was prepared from PS69D1 (B.t. PS69D1) as disclosed in Example 3. RFLP analyses were performed by standard hybridization of Southern blots of PS69D1 DNA with a 32P-labeled oligonucleotide probe designated as 69D1-D. The sequence of the 69D1-D probe was:

5' AAA CAT ATT AGA TTA GCA CAT ATT TTF GCA ACA CAA AA 3' (SEQ ID NO. 26) Hybridizing bands included an approximately 2.0 kbp HindIII fragment.

A gene library was constructed from PS69D1DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega, Madison, WI). Recombinant phage were packaged and plated on E. coli KW251 cells (Promega, Madison, Wis.). Plaques were screened by hybridization with the radiolabeled 69D1-D oligonucleotide probe. Hybridizing phage were plaque-purified and used to infect liquid cultures of E. coli KW251 cells for isolation of phage DNA by standard procedures (Maniatis et al. [1982] Molecular Cloning. A Laboratory Manual, Cold Spring Harbor, N.Y.). For subcloning, preparative amounts of DNA were digested with HindIII and electrophoresed on an agarose gel. The approximately, 2.0 kbp band containing the toxin gene was excised from the gel, electroeluted from the gel slice, and purified by ion exchange chromatography as above. The purified DNA insert was ligated into HindIII-digested pHTBlueII (and E. coil/B.t. shuttle vector comprised of pBluescript S/K (Stratagene, San Diego, Calif.) and the replication origin from a resident B.t. plasmid (D. Lereclus et al [1989] FEMS Microbiol. Lett. 60:211–218). The ligation mix was used to transform frozen, competent E. coli NM522 cells (ATCC 47000). Transformants were plated on LB agar containing 5-bromo-4-chloro-3-indolyl-(Beta)-D-galactoside (XGAL). Plasmids were purified from putative recombinants by alkaline lysis (Maniatis et al., supra) and analyzed by electrophoresis of HindIII digests on agarose gels. The desired plasmid construct, pMYC2317, contains a toxin gene that is novel compared to the maps of other toxin genes encoding insecticidal proteins.

EXAMPLE 8

Molecular Cloning of a Gene Encoding a Novel Toxin from Bacillus thuringiensis Strain PS63B Example 2 shows the aminoterminal and internal polypeptide sequences of the PS63B toxin protein as determined by standard Edman protein sequencing. From these sequences, two oligonucleotide primers were designed using a codon frequency table assembled from B.t. genes encoding δ-endotoxins. The sequence of the forward primer (63B-A) was complementary to the predicted DNA sequence at the 5' end of the gene:

63B-A-5' CAA T/CTA CAA GCA/T CAA CC 3' (SEQ ID NO. 27)

The sequence of the reverse primer (63B-INT) was complementary to the inverse of the internal predicted DNA sequence:

63B-INT-5' TTC ATC TAA AAT TCT TTG A/TAC 3' (SEQ ID NO. 28)

These primers were used in standard polymerase chain reactions (Cetus Corporation) to amplify an approximately 460 bp fragment of the 63B toxin gene for use as a DNA cloning probe. Standard Southern blots of total cellular DNA from PS63B were hybridized with the radiolabeled PCR probe. Hybridizing bands included an approximately 4.4 kbp XbaI fragment, an approximately 2.0 kbp HindIII fragment, and an approximately 6.4 kbp SpeI fragment.

Total cellular DNA was prepared from Bacillus thuringiensis (B.t.) cells grown to an optical density of 1.0 at 600 nm. The cells were recovered by centrifugation and protoplasts were prepared in lysis mix (300 mM sucrose, 25 mM Tris-HCl, 25 mM EDTA, pH=8.0) and lysozyme at a concentration of 20 mg/ml. The protoplasts were ruptured by addition of ten volumes of 0.1M NaCl, 0.1M Tris-HCl pH 8.0, and 0.1% SDS. The cellular material was quickly frozen at −70° C. and thawed to 37° C. twice. The supernatant was extracted twice with phenol/chloroform (1:1). The nucleic acids were precipitated with ethanol. To remove as much RNA as possible from the DNA preparation, RNase at final concentration of 200 µg/ml was added. After incubation at 37° C. for 1 hour, the solution was extracted once with phenol/chloroform and precipitated with ethanol.

A gene library was constructed from PS63B total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, NH). The isolated NdeII fragments were ligated into BamHI-digested LambdaGEM-11 (PROMEGA). The packaged phage were plated on *E. coli* KW251 cells (PROMEGA) at a high titer and screened using the radiolabeled approximately 430 bp fragment probe amplified with the 63B-A and 63B internal primers (SEQ ID NOS. 27 and 28, respectively) by polymerase chain reaction. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis et al., supra). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli/B.t.* shuttle vector comprised of pBlueScript S/K [Stratagene, San Diego, Calif.] and the replication origin from a resident *B.t.* plasmid [Lereclus, D. et al. (1989) FEMS Microbiol. Lett. 60:211–218]). The ligation mix was introduced by transformation into competent *E. coli* NM522 cells (ATCC 47000) and plated on LB agar containing ampicillin (100 μg/ml), IPTG (2%), and XGAL (2%). White colonies, with putative restriction fragment insertions in the (Beta)-galactosidase gene of pHTBlueII, were subjected to standard rapid plasmid purification procedures (Maniatis et al., supra). Plasmids ere analyzed by SalI digestion and agarose gel electrophoresis. The desired plasmid construct, pMYC1641, contains an approximately 14 kb SalI insert.

For subcloning, preparative amounts of DNA were digested with XbaI and electrophoresed on an agarose gel. The approximately 4.4 kbp band containing the toxin gene was excised from the gel, electroeluted from the gel slice, and purified by ion exchange chromatography as above. This fragment was ligated into XbaI cut pHTBlueII and the resultant plasmid was designated pMYC1642.

EXAMPLE 9

Cloning of a Novel Toxin Gene From *B.t.* PS33F2 and Transformation into *Escherichia coli*

Total cellular DNA was prepared from *B.t.* PS33F2 cells grown to an optical density, at 600 nm, of 1.0. Cells were pelleted by centrifugation and resuspended in protoplast buffer (20 mg/ml lysozyme in 0.3M sucrose, 25 mM Tris-Cl [pH 8.0], 25 mM EDTA). After incubation at 37° C. for 1 hour, protoplasts were lysed by the addition of nine volumes of a solution of 0.1M NaCl, 0.1% SDS, 0.1M Tris-Cl followed by two cycles of freezing and thawing. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE) and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Plasmid DNA was extracted from protoplasts prepared as described above. Protoplasts were lysed by the addition of nine volumes of a solution of 10 mM Tris-Cl, 1 mM EDTA, 0.085 N NaOH, 0.1% SDS, pH=8.0. SDS was added to 1% final concentration to complete lysis. One-half volume of 3M KOAc was then added and the cellular material was precipitated overnight at 4° C. After centrifugation, the DNA was precipitated with ethanol and plasmids were purified by isopycnic centrifugation on cesium chloride-ethidium bromide gradients.

Restriction Fragment Length Polymorphism (RFLP) analyses were performed by standard hybridization of Southern blots of PS33F2 plasmid and total cellular DNA with $^{32}P$-labelled oligonucleotide probes designed to the N-terminal amino acid sequence disclosed in Example 2.

Probe 33F2A: 5' GCA/T ACA/T TTA AAT GAA GTA/T TAT 3' (SEQ ID NO. 33)

Probe 33F2B: 5' AAT GAA GTA/T TAT CCA/T GTA/T AAT 3' (SEQ ID NO. 34)

Hybridizing bands included an approximately 5.85 kbp EcoRI fragment. Probe 33F2A and a reverse PCR primer were used to amplify a DNA fragment of approximately 1.8 kbp for use as a hybridization probe for cloning the PS33F2 toxin gene. The sequence of the reverse primer was:

5' GCAAGCGGCCGCTTATGGAATAAATTCAATT C/T T/G A/G TC T/A A 3' (SEQ ID NO. 35).

A gene library was constructed from PS33F2 plasmid DNA digested with EcoRI. Restriction digests were fractionated by agarose gel electrophoresis. DNA fragments 4.3–6.6 kbp were excised from the gel, electroeluted from the gel slice, and recovered by ethanol precipitation after purification on an Elutip-D ion exchange column (Schleicher and Schuel, Keene N.H.). The EcoRI inserts were ligated into EcoRI-digested pHTBlueII (an *E. coli/B. thuringiensis* shuttle vector comprised of pBluescript S/K [Stratagene] and the replication origin from a resident *B.t.* plasmid [D. Lereclus et al. 1989. FEMS Microbial. Lett. 60:211–218]). The ligation mixture was transformed into frozen, competent NM522 cells (ATCC 47000). Transformants were plated on LB agar containing ampicillin, isopropyl-(Beta)-D-thiogalactoside (IPTG), and 5-bromo-4-chloro-3-indolyl-(Beta)-D-galactoside (XGAL). Colonies were screened by hybridization with the radiolabeled PCR amplified probe described above. Plasmids were purified from putative toxin gene clones by alkaline lysis and analyzed by agarose gel electrophoresis of restriction digests. The desired plasmid construct, pMYC2316, contains an approximately 5.85 kbp Eco4RI insert; the toxin gene residing on this DNA fragment (33F2a) is novel compared to the DNA sequences of other toxin genes encoding nematicidal proteins.

Plasmid pMYC2316 was introduced into the acrystalliferous (Cry-) *B.t.* host, HD-1 CryB (A. Aronson, Purdue University, West Lafayette, Ind.) by electroporation. Expression of an approximately 120–140 kDa crystal protein was verified by SDS-PAGE analysis. Crystals were purified on NaBr gradients (M.A. Pfannenstiel et al. 1984. FEMS Microbiol. Lett. 21:39) for determination of toxicity of the cloned gene product to *Pratylenchus spp.*

EXAMPLE 10

Activity of the *B.t.* Gene Product 33F2 Against the Plant Nematode *Pratylenchus* spp.

*Pratylenchus* spp. was reared aseptically on excised corn roots in Gamborg's B5 medium (GIBCO® Laboratories, Grand Island, N.Y.) Bioassays were done in 24 well assay plates (Corning #25820) using L 3–4 larvae as described by Tsai and van Gundy (J. Nematol. 22(3):327–332). Approximately 20 nematodes were placed in each well. A total of 80–160 nematodes were used in each treatment. Samples of protein were suspended in an aqueous solution using a hand-held Dounce homogenizer.

Mortality was assessed visually 3 days after treatment. Larvae that were nearly straight and not moving were considered moribund. Representative results are as follows:

| 33F2a (ppm) | % Moribund |
|---|---|
| 0 | 12 |
| 75 | 78 |

Species of Pratylenchus, for example *P. scribneri*, are known pathogens of many economically important crops including corn, peanuts, soybean, alfalfa, beans, tomato, and citrus. These "root lesion" nematodes are the second most economically damaging genus of plant parasitic nematodes (after Meloidogyne-the "root knot" nematode), and typify the migratory endoparasites.

EXAMPLE 11

Cloning of Novel Nematode-Active Genes Using Generic Oligonucleotide Primers The nematicidal gene of a new nematicidal *B.t.* can be obtained from DNA of the strain by performing the standard polymerase chain reaction procedure as in Example 8 using the oligonucleotides of SEQ ID NO. 32 or SEQ ID NO. 30 as reverse primers and SEQ ID NO. 14, SEQ ID NO. 16, SEQ ID NO. 24, Probe B of SEQ ID NO. 5 (AAT GAA GTA/T TAT CCA/T GTA/T AAT), or SEQ ID NO. 27 as forward primers. The expected PCR fragments would be approximately 330 to 600 bp (with either reverse primer and SEQ ID NO. 14), 1000 to 1400 bp (with either reverse primer and SEQ ID NO. 16), and 1800 to 2100 bp (with either reverse primer and any of the three N-terminal primers, SEQ ID NO. 5 (Probe B), SEQ ID NO. 24, and SEQ ID NO. 27). Alternatively, a complement from the primer family described by SEQ ID NO. 14 can be used as reverse primer with SEQ ID NO. 16, SEQ ID NO. 24, SEQ ID NO. 5 (Probe B), or SEQ ID NO. 27 as forward primers. The expected PCR fragments would be approximately 650 to 1000 bp with SEQ ID NO. 16, and 1400 to 1800 bp (for the three N-terminal primers, SEQ ID NO. 5 (Probe B), SEQ ID NO. 24, and SEQ ID NO. 27). Amplified DNA fragments of the indicated sizes can be radiolabeled and used as probes to clone the entire gene as in Example 8.

EXAMPLE 12

Further Cloning of Novel Nematode-Active Genes Using Generic Oligonucleotide Primers A gene coding for a nematicidal toxin a new nematicidal *B.t.* isolate can also be obtained from DNA of the strain by performing the standard polymerase chain reaction procedure as in Example 8 using oligonucleotides derived from the PS52A1 and PS69D1 gene sequences as follows:

1. Forward primer "TGATTTT(T or A)(C or A)TCAATTATAT(A or G)A(G or T)GTTTAT" (SEQ ID NO. 36) can be used with primers complementary to probe "AAGAGTTA(C or T)TA(A or G)A(G or A)AAAGTA" (SEQ ID NO. 37), probe "TTAGGACCATT(A or G)(C or T)T(T or A)GGATTTGTTGT(A or T)TATGAAAT" (SEQ ID NO. 38), and probe "GA(C or T)AGAGATGT(A or T)AAAAT(C or T)(T or A)TAGGAATG" (SEQ ID NO. 39) to produce amplified fragments of approximately 440, 540, and 650 bp, respectively.

2. Forward primer "TT(A or C)TTAAA(A or T)C(A or T)GCTAATGATATT" (SEQ ID NO. 40) can be used with primers complementary to SEQ ID NO. 37, SEQ ID NO. 38, and SEQ ID NO. 39 to produce amplified fragments of approximately 360, 460, and 570 bp, respectively.

3. Forward primer SEQ ID NO. 37 can be used with primers complementary to SEQ ID NO. 38 and SEQ ID NO. 39 to produce amplified fragments of approximately 100 and 215 bp, respectively.

Amplified DNA fragments of the indicated sizes can be radiolabeled and used as probes to clone the entire gene as in Example 8.

EXAMPLE 13

Insertion of Toxin Gene Into Plants

One aspect of the subject invention is the transformation of plants with genes coding for a nematicidal toxin. The transformed plants are resistant to attack by nematodes.

Genes coding for nematicidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence coding for the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., Crit. Rev. Plant Sci. 4:1–46; and An et al. (1985) EMBO J. 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] Mol. Gen. Genet. 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotide sequence comprising a nucleotide sequence which encodes a toxin active against nematodes wherein said toxin comprises an amino acid sequence selected from the group consisting of SEQ ID NO. 6, SEQ ID NO. 12, SEQ ID NO. 10, and fragments of SEQ ID NO. 6, SEQ ID NO. 12, or SEQ ID NO. 10 which maintain pesticidal activity against nematodes.

2. The nucleotide sequence of claim 1, wherein said nucleotide sequence encodes the 33F2 toxin having the amino acid sequence shown in SEQ ID NO. 6, or fragments thereof which maintain pesticidal activity against nematodes.

3. The nucleotide sequence of claim 1, wherein said nucleotide sequence encodes the 63B toxin having the amino acid sequence shown in SEQ ID NO. 12, or fragments thereof which maintain pesticidal activity against nematodes.

4. The nucleotide sequence of claim 1, wherein said nucleotide sequence encodes the 69D1 toxin having the amino acid sequence shown in SEQ ID NO. 10, or fragments thereof which maintain pesticidal activity against nematodes.

5. The nucleotide sequence of claim 2, comprising the nucleotide sequence of SEQ ID NO. 5.

6. The nucleotide sequence of claim 3, comprising the nucleotide sequence of SEQ ID NO. 11.

7. The nucleotide sequence of claim 4, comprising the nucleotide sequence of SEQ ID NO. 9.

8. A heterologous transformmed host cell comprising a nucleotide sequence as defined in claim 1.

* * * * *

UNITED STATES PATENT AND TRADEMARK OFFICE
CERTIFICATE OF CORRECTION

PATENT NO. : 5,753,492
DATED : May 19, 1998
INVENTOR(S) : Schnepf et al.

It is certified that error appears in the above-identified patent and that said Letters Patent is hereby corrected as shown below:

Column 1, line 50: "colubfifonmis" should read --colubriformis--;

line 63: "prelirminary" should read --preliminary--; and line 64: "thuningiensis" should read --thuringiensis--.

Column 4, bottom, 2nd line of 201: "BxxxxxxxxX XXXXO LXXXK" should read

--BxxxxxxxxX XXXXOLXXXK--.

Column 5, top, 2nd line of 501: "XXXXUXLZXX" should read --XXXXUXLZXX--.

Column 7, line 35: "(CryhIIIA" should read --(CryIIIA;--.

Column 10, line 39: "AR" should read --AII--.

Column 13, line 14: "Tfhchonema" should read --Trichonema--;

line 25: "Diiylenchus" should read --Ditylenchus--;

Column 15, line 8: "Melioti Alcaligenes" should read --melioti, Alcaligenes--; and line 39: "Eschenichia" should read --Escherichia--.

UNITED STATES PATENT AND TRADEMARK OFFICE
CERTIFICATE OF CORRECTION

PATENT NO. : 5,753,492
DATED : May 19, 1998
INVENTOR(S) : Schnepf et al.

It is certified that error appears in the above-identified patent and that said Letters Patent is hereby corrected as shown below:

Column 16, line 3: "Pseudomonasfluorescens" should read --Pseudomonas fluorescens--;

lines 4-5: "thutingiensis, Eschenchia coli Bacillus" should read

--*thuringiensis, Escherichia coli, Bacillus*--.

Column 18, line 67: "Elutip™ m ion" should read --Elutip™ ion--.

Column 20, line 36: "TCAIT" should read --TCA/T--;

line 36: "ACA[T" should read --ACA/T--; and line 61: "Thuringiensis" should read --thuringiensis--.

Column 21, line 52: "TTF" should read --TTT--; and line 55: "PS69D1DNA" should read --PS69D1 DNA--.

UNITED STATES PATENT AND TRADEMARK OFFICE
CERTIFICATE OF CORRECTION

PATENT NO. : 5,753,492
DATED : May 19, 1998
INVENTOR(S) : Schnepf et al.

It is certified that error appears in the above-identified patent and that said Letters Patent is hereby corrected as shown below:

Column 22, line 2: "*Cloning.*" should read --*Cloning:*--;

line 54: "Tris-HCI" should read --Tris-HC1--; and line 56: "Tris-HCI" should read --Tris-HCl--.

Column 26, line 61: "Agrobactenium" should read --Agrobacterium--.

Signed and Sealed this

Sixteenth Day of February, 1999

Attest:

*Acting Commissioner of Patents and Trademarks*

Attesting Officer

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 4155 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: PS17
        ( C ) INDIVIDUAL ISOLATE: PS17a ( v i i ) IMMEDIATE SOURCE:
        ( B ) CLONE: E. coli NM522(pMYC 1627) NRRL B-18651

( x i ) SEQUENCE DESCRIPTION: SEQ ID NO:1:

ATGGCAATTT TAAATGAATT ATATCCATCT GTACCTTATA ATGTATTGGC GTATACGCCA 60

CCCTCTTTTT TACCTGATGC GGGTACACAA GCTACACCTG CTGACTTAAC AGCTTATGAA 120

CAATTGTTGA AAAATTTAGA AAAAGGGATA AATGCTGGAA CTTATTCGAA AGCAATAGCT 180

GATGTACTTA AAGGTATTTT TATAGATGAT ACAATAAATT ATCAAACATA TGTAAATATT 240

GGTTTAAGTT TAATTACATT AGCTGTACCG GAAATTGGTA TTTTTACACC TTTCATCGGT 300

TTGTTTTTTG CTGCATTGAA TAAACATGAT GCTCCACCTC CTCCTAATGC AAAAGATATA 360

TTTGAGGCTA TGAAACCAGC GATTCAAGAG ATGATTGATA GAACTTTAAC TGCGGATGAG 420

CAAACATTTT TAAATGGGGA AATAAGTGGT TTACAAAATT TAGCAGCAAG ATACCAGTCT 480

ACAATGGATG ATATTCAAAG CCATGGAGGA TTTAATAAGG TAGATTCTGG ATTAATTAAA 540

AAGTTTACAG ATGAGGTACT ATCTTTAAAT AGTTTTTATA CAGATCGTTT ACCTGTATTT 600

ATTACAGATA ATACAGCGGA TCGAACTTTG TTAGGTCTTC CTTATTATGC TATACTTGCG 660

```
AGCATGCATC TTATGTTATT AAGAGATATC ATTACTAAGG GTCCGACATG GGATTCTAAA        720
ATTAATTTCA CACCAGATGC AATTGATTCC TTTAAAACCG ATATTAAAAA TAATATAAAG        780
CTTTACTCTA AAACTATTTA TGACGTATTT CAGAAGGGAC TTGCTTCATA CGGAACGCCT        840
TCTGATTTAG AGTCCTTTGC AAAAAAACAA AAATATATTG AAATTATGAC AACACATTGT        900
TTAGATTTTG CAAGATTGTT TCCTACTTTT GATCCAGATC TTTATCCAAC AGGATCAGGT        960
GATATAAGTT TACAAAAAAC ACGTAGAATT CTTTCTCCTT TTATCCCTAT ACGTACTGCA       1020
GATGGGTTAA CATTAAATAA TACTTCAATT GATACTTCAA ATTGGCCTAA TTATGAAAAT       1080
GGGAATGGCG CGTTTCCAAA CCCAAAAGAA AGAATATTAA AACAATTCAA ACTGTATCCT       1140
AGTTGGAGAG CGGGACAGTA CGGTGGGCTT TTACAACCTT ATTTATGGGC AATAGAAGTC       1200
CAAGATTCTG TAGAGACTCG TTTGTATGGG CAGCTTCCAG CTGTAGATCC ACAGGCAGGG       1260
CCTAATTATG TTTCCATAGA TTCTTCTAAT CCAATCATAC AAATAAATAT GGATACTTGG       1320
AAAACACCAC CACAAGGTGC GAGTGGGTGG AATACAAATT TAATGAGAGG AAGTGTAAGC       1380
GGGTTAAGTT TTTTACAACG AGATGGTACG AGACTTAGTG CTGGTATGGG TGGTGGTTTT       1440
GCTGATACAA TATATAGTCT CCCTGCAACT CATTATCTTT CTTATCTCTA TGGAACTCCT       1500
TATCAAACTT CTGATAACTA TTCTGGTCAC GTTGGTGCAT TGGTAGGTGT GAGTACGCCT       1560
CAAGAGGCTA CTCTTCCTAA TATTATAGGT CAACCAGATG AACAGGGAAA TGTATCTACA       1620
ATGGGATTTC CGTTTGAAAA AGCTTCTTAT GGAGGTACAG TTGTTAAAGA ATGGTTAAAT       1680
GGTGCGAATG CGATGAAGCT TTCTCCTGGG CAATCTATAG GTATTCCTAT TACAAATGTA       1740
ACAAGTGGAG AATATCAAAT TCGTTGTCGT TATGCAAGTA ATGATAATAC TAACGTTTTC       1800
TTTAATGTAG ATACTGGTGG AGCAAATCCA ATTTTCCAAC AGATAAACTT TGCATCTACT       1860
GTAGATAATA ATACGGGAGT ACAAGGAGCA AATGGTGTCT ATGTAGTCAA ATCTATTGCT       1920
ACAACTGATA ATTCTTTTAC AGAAATTCCT GCGAAGACGA TTAATGTTCA TTTAACCAAC       1980
CAAGGTTCTT CTGATGTCTT TTTAGACCGT ATTGAATTTA TACCTTTTTC TCTACCTCTT       2040
ATATATCATG GAAGTTATAA TACTTCATCA GGTGCAGATG ATGTTTATG GTCTTCTTCA        2100
AAATGAATT ACTACGATAT AATAGTAAAT GGTCAGGCCA ATAGTAGTAG TATCGCTAGT        2160
TCTATGCATT TGCTTAATAA AGGAAAAGTG ATAAAAACAA TTGATATTCC AGGGCATTCG       2220
GAAACCTTCT TTGCTACGTT CCCAGTTCCA GAAGGATTTA ATGAAGTTAG AATTCTTGCT       2280
GGCCTTCCAG AAGTTAGTGG AAATATTACC GTACAATCTA ATAATCCGCC TCAACCTAGT       2340
AATAATGGTG GTGGTGATGG TGGTGGTAAT GGTGGTGGTG ATGGTGGTCA ATACAATTTT       2400
TCTTTAAGCG GATCTGATCA TACGACTATT TATCATGGAA AACTTGAAAC TGGGATTCAT       2460
GTACAAGGTA ATTATACCTA TACAGGTACT CCCGTATTAA TACTGAATGC TTACAGAAAT       2520
AATACTGTAG TATCAAGCAT TCCAGTATAT TCTCCTTTTG ATATAACTAT ACAGACAGAA       2580
GCTGATAGCC TTGAGCTTGA ACTACAACCT AGATATGGTT TTGCCACAGT GAATGGTACT       2640
GCAACAGTAA AAAGTCCTAA TGTAAATTAC GATAGATCAT TTAAACTCCC AATAGACTTA       2700
CAAAATATCA CAACACAAGT AAATGCATTA TTCGCATCTG GAACACAAAA TATGCTTGCT       2760
CATAATGTAA GTGATCATGA TATTGAAGAA GTTGTATTAA AAGTGGATGC CTTATCAGAT       2820
GAAGTATTTG GAGATGAGAA GAAGGCTTTA CGTAAATTGG TGAATCAAGC AAAACGTTTG       2880
AGTAGAGCAA GAAATCTTCT GATAGGTGGG AGTTTGAAA ATTGGGATGC ATGGTATAAA        2940
GGAAGAAATG TAGTAACTGT ATCTGATCAT GAACTATTTA AGAGTGATCA TGTATTATTA       3000
CCACCACCAG GATTGTCTCC ATCTTATATT TTCCAAAAAG TGGAGGAATC TAAATTAAAA       3060
```

-continued

```
CCAAATACAC GTTATATTGT TTCTGGATTC ATCGCACATG GAAAAGACCT AGAAATTGTT      3120

GTTTCACGTT ATGGGCAAGA AGTGCAAAAG GTCGTGCAAG TTCCTTATGG AGAAGCATTC      3180

CCGTTAACAT CAAATGGACC AGTTTGTTGT CCCCCACGTT CTACAAGTAA TGGAACCTTA      3240

GGAGATCCAC ATTTCTTTAG TTACAGTATC GATGTAGGTG CACTAGATTT ACAAGCAAAC      3300

CCTGGTATTG AATTTGGTCT TCGTATTGTA AATCCAACTG GAATGGCACG CGTAAGCAAT      3360

TTGGAAATTC GTGAAGATCG TCCATTAGCA GCAAATGAAA TACGACAAGT ACAACGTGTC      3420

GCAAGAAATT GGAGAACCGA GTATGAGAAA GAACGTGCGG AAGTAACAAG TTTAATTCAA      3480

CCTGTTATCA ATCGAATCAA CGGATTGTAT GAAAATGGAA ATTGGAACGG TTCTATTCGT      3540

TCAGATATTT CGTATCAGAA TATAGACGCG ATTGTATTAC CAACGTTACC AAAGTTACGC      3600

CATTGGTTTA TGTCAGATAG ATTCAGTGAA CAAGGAGATA TAATGGCTAA ATTCCAAGGT      3660

GCATTAAATC GTGCGTATGC ACAACTGGAA CAAAGTACGC TTCTGCATAA TGGTCATTTT      3720

ACAAAAGATG CAGCTAATTG GACAATAGAA GGCGATGCAC ATCAGATAAC ACTAGAAGAT      3780

GGTAGACGTG TATTGCGACT TCCAGATTGG TCTTCGAGTG TATCTCAAAT GATTGAAATC      3840

GAGAATTTTA ATCCAGATAA AGAATACAAC TTAGTATTCC ATGGGCAAGG AGAAGGAACG      3900

GTTACGTTGG AGCATGGAGA AGAAACAAAA TATATAGAAA CGCATACACA TCATTTTGCG      3960

AATTTTACAA CTTCTCAACG TCAAGGACTC ACGTTTGAAT CAAATAAAGT GACAGTGACC      4020

ATTTCTTCAG AAGATGGAGA ATTCTTAGTG GATAATATTG CGCTTGTGGA AGCTCCTCTT      4080

CCTACAGATG ACCAAAATTC TGAGGGAAAT ACGGCTTCCA GTACGAATAG CGATACAAGT      4140

ATGAACAACA ATCAA                                                     4155
```

( 2 ) INFORMATION FOR SEQ ID NO:2:

( i ) SEQUENCE CHARACTERISTICS:
        ( A ) LENGTH: 1385 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v ) ORIGINAL SOURCE:
        ( A ) ORGANISM: BACILLUS THURINGIENSIS
        ( C ) INDIVIDUAL ISOLATE: PS17

( v i i ) IMMEDIATE SOURCE:
        ( B ) CLONE: E. coli NM522(pMYC 1627) NRRL B-18651

( x i ) SEQUENCE DESCRIPTION: SEQ ID NO:2:

Met Ala Ile Leu Asn Glu Leu Tyr Pro Ser Val Pro Tyr Asn Val Leu
1 5 10 15

Ala Tyr Thr Pro Pro Ser Phe Leu Pro Asp Ala Gly Thr Gln Ala Thr
20 25 30

Pro Ala Asp Leu Thr Ala Tyr Glu Gln Leu Leu Lys Asn Leu Glu Lys
35 40 45

Gly Ile Asn Ala Gly Thr Tyr Ser Lys Ala Ile Ala Asp Val Leu Lys
50 55 60

Gly Ile Phe Ile Asp Asp Thr Ile Asn Tyr Gln Thr Tyr Val Asn Ile
65 70 75 80

Gly Leu Ser Leu Ile Thr Leu Ala Val Pro Glu Ile Gly Ile Phe Thr
85 90 95

| | | | | | | | | | | | | | | |
|---|---|---|---|---|---|---|---|---|---|---|---|---|---|---|
|Pro|Phe|Ile|Gly 100|Leu|Phe|Phe|Ala|Ala 105|Leu|Asn|Lys|His|Asp 110|Ala|Pro|
|Pro|Pro|Pro 115|Asn|Ala|Lys|Asp|Ile 120|Phe|Glu|Ala|Met|Lys 125|Pro|Ala|Ile|
|Gln|Glu 130|Met|Ile|Asp|Arg|Thr 135|Leu|Thr|Ala|Asp|Glu 140|Gln|Thr|Phe|Leu|
|Asn 145|Gly|Glu|Ile|Ser|Gly 150|Leu|Gln|Asn|Leu|Ala 155|Ala|Arg|Tyr|Gln|Ser 160|
|Thr|Met|Asp|Asp|Ile 165|Gln|Ser|His|Gly|Gly 170|Phe|Asn|Lys|Val|Asp 175|Ser|
|Gly|Leu|Ile|Lys 180|Lys|Phe|Thr|Asp|Glu 185|Val|Leu|Ser|Leu|Asn 190|Ser|Phe|
|Tyr|Thr|Asp 195|Arg|Leu|Pro|Val|Phe 200|Ile|Thr|Asp|Asn|Thr 205|Ala|Asp|Arg|
|Thr|Leu 210|Leu|Gly|Leu|Pro|Tyr 215|Tyr|Ala|Ile|Leu|Ala 220|Ser|Met|His|Leu|
|Met 225|Leu|Leu|Arg|Asp|Ile 230|Ile|Thr|Lys|Gly|Pro 235|Thr|Trp|Asp|Ser|Lys 240|
|Ile|Asn|Phe|Thr|Pro 245|Asp|Ala|Ile|Asp|Ser 250|Phe|Lys|Thr|Asp|Ile 255|Lys|
|Asn|Asn|Ile|Lys 260|Leu|Tyr|Ser|Lys|Thr 265|Ile|Tyr|Asp|Val|Phe 270|Gln|Lys|
|Gly|Leu|Ala 275|Ser|Tyr|Gly|Thr|Pro 280|Ser|Asp|Leu|Glu|Ser 285|Phe|Ala|Lys|
|Lys|Gln 290|Lys|Tyr|Ile|Glu|Ile 295|Met|Thr|Thr|His|Cys 300|Leu|Asp|Phe|Ala|
|Arg 305|Leu|Phe|Pro|Thr|Phe 310|Asp|Pro|Asp|Leu|Tyr 315|Pro|Thr|Gly|Ser|Gly 320|
|Asp|Ile|Ser|Leu|Gln 325|Lys|Thr|Arg|Arg|Ile 330|Leu|Ser|Pro|Phe|Ile 335|Pro|
|Ile|Arg|Thr|Ala 340|Asp|Gly|Leu|Thr|Leu 345|Asn|Asn|Thr|Ser|Ile 350|Asp|Thr|
|Ser|Asn|Trp 355|Pro|Asn|Tyr|Glu|Asn 360|Gly|Asn|Gly|Ala|Phe 365|Pro|Asn|Pro|
|Lys|Glu 370|Arg|Ile|Leu|Lys|Gln 375|Phe|Lys|Leu|Tyr|Pro 380|Ser|Trp|Arg|Ala|
|Gly 385|Gln|Tyr|Gly|Gly|Leu 390|Leu|Gln|Pro|Tyr|Leu 395|Trp|Ala|Ile|Glu|Val 400|
|Gln|Asp|Ser|Val|Glu 405|Thr|Arg|Leu|Tyr|Gly 410|Gln|Leu|Pro|Ala|Val 415|Asp|
|Pro|Gln|Ala|Gly 420|Pro|Asn|Tyr|Val|Ser 425|Ile|Asp|Ser|Ser|Asn 430|Pro|Ile|
|Ile|Gln|Ile|Asn 435|Met|Asp|Thr|Trp|Lys 440|Thr|Pro|Pro|Gln|Gly 445|Ala|Ser|
|Gly|Trp 450|Asn|Thr|Asn|Leu|Met 455|Arg|Gly|Ser|Val|Ser 460|Gly|Leu|Ser|Phe|
|Leu 465|Gln|Arg|Asp|Gly|Thr 470|Arg|Leu|Ser|Ala|Gly 475|Met|Gly|Gly|Gly|Phe 480|
|Ala|Asp|Thr|Ile|Tyr 485|Ser|Leu|Pro|Ala|Thr 490|His|Tyr|Leu|Ser|Tyr 495|Leu|
|Tyr|Gly|Thr|Pro 500|Tyr|Gln|Thr|Ser|Asp 505|Asn|Tyr|Ser|Gly|His 510|Val|Gly|
|Ala|Leu|Val|Gly|Val|Ser|Thr|Pro|Gln|Glu|Ala|Thr|Leu|Pro|Asn|Ile|

-continued

|     | 515 |     |     |     |     | 520 |     |     |     |     | 525 |     |     |     |
|-----|-----|-----|-----|-----|-----|-----|-----|-----|-----|-----|-----|-----|-----|-----|
| Ile | Gly | Gln | Pro | Asp | Glu | Gln | Gly | Asn | Val | Ser | Thr | Met | Gly | Phe | Pro |
|     |     | 530 |     |     |     | 535 |     |     |     | 540 |     |     |     |     |
| Phe | Glu | Lys | Ala | Ser | Tyr | Gly | Gly | Thr | Val | Val | Lys | Glu | Trp | Leu | Asn |
| 545 |     |     |     |     | 550 |     |     |     | 555 |     |     |     |     |     | 560 |
| Gly | Ala | Asn | Ala | Met | Lys | Leu | Ser | Pro | Gly | Gln | Ser | Ile | Gly | Ile | Pro |
|     |     |     |     | 565 |     |     |     |     | 570 |     |     |     | 575 |     |     |
| Ile | Thr | Asn | Val | Thr | Ser | Gly | Glu | Tyr | Gln | Ile | Arg | Cys | Arg | Tyr | Ala |
|     |     |     | 580 |     |     |     |     | 585 |     |     |     |     | 590 |     |     |
| Ser | Asn | Asp | Asn | Thr | Asn | Val | Phe | Phe | Asn | Val | Asp | Thr | Gly | Gly | Ala |
|     |     | 595 |     |     |     |     | 600 |     |     |     |     | 605 |     |     |     |
| Asn | Pro | Ile | Phe | Gln | Gln | Ile | Asn | Phe | Ala | Ser | Thr | Val | Asp | Asn | Asn |
|     | 610 |     |     |     |     | 615 |     |     |     |     | 620 |     |     |     |     |
| Thr | Gly | Val | Gln | Gly | Ala | Asn | Gly | Val | Tyr | Val | Val | Lys | Ser | Ile | Ala |
| 625 |     |     |     |     | 630 |     |     |     | 635 |     |     |     |     |     | 640 |
| Thr | Thr | Asp | Asn | Ser | Phe | Thr | Glu | Ile | Pro | Ala | Lys | Thr | Ile | Asn | Val |
|     |     |     |     | 645 |     |     |     |     | 650 |     |     |     |     | 655 |     |
| His | Leu | Thr | Asn | Gln | Gly | Ser | Ser | Asp | Val | Phe | Leu | Asp | Arg | Ile | Glu |
|     |     |     | 660 |     |     |     |     | 665 |     |     |     |     | 670 |     |     |
| Phe | Ile | Pro | Phe | Ser | Leu | Pro | Leu | Ile | Tyr | His | Gly | Ser | Tyr | Asn | Thr |
|     |     | 675 |     |     |     |     | 680 |     |     |     |     | 685 |     |     |     |
| Ser | Ser | Gly | Ala | Asp | Asp | Val | Leu | Trp | Ser | Ser | Ser | Asn | Met | Asn | Tyr |
|     | 690 |     |     |     |     | 695 |     |     |     |     | 700 |     |     |     |     |
| Tyr | Asp | Ile | Ile | Val | Asn | Gly | Gln | Ala | Asn | Ser | Ser | Ser | Ile | Ala | Ser |
| 705 |     |     |     |     | 710 |     |     |     |     | 715 |     |     |     |     | 720 |
| Ser | Met | His | Leu | Leu | Asn | Lys | Gly | Lys | Val | Ile | Lys | Thr | Ile | Asp | Ile |
|     |     |     |     | 725 |     |     |     |     | 730 |     |     |     |     | 735 |     |
| Pro | Gly | His | Ser | Glu | Thr | Phe | Phe | Ala | Thr | Phe | Pro | Val | Pro | Glu | Gly |
|     |     |     | 740 |     |     |     |     | 745 |     |     |     |     | 750 |     |     |
| Phe | Asn | Glu | Val | Arg | Ile | Leu | Ala | Gly | Leu | Pro | Glu | Val | Ser | Gly | Asn |
|     |     | 755 |     |     |     |     | 760 |     |     |     |     | 765 |     |     |     |
| Ile | Thr | Val | Gln | Ser | Asn | Asn | Pro | Pro | Gln | Pro | Ser | Asn | Asn | Gly | Gly |
|     | 770 |     |     |     |     | 775 |     |     |     |     | 780 |     |     |     |     |
| Gly | Asp | Gly | Gly | Gly | Asn | Gly | Gly | Asp | Gly | Gly | Gln | Tyr | Asn | Phe |
| 785 |     |     |     |     | 790 |     |     |     | 795 |     |     |     |     | 800 |
| Ser | Leu | Ser | Gly | Ser | Asp | His | Thr | Thr | Ile | Tyr | His | Gly | Lys | Leu | Glu |
|     |     |     |     | 805 |     |     |     |     | 810 |     |     |     |     | 815 |     |
| Thr | Gly | Ile | His | Val | Gln | Gly | Asn | Tyr | Thr | Tyr | Thr | Gly | Thr | Pro | Val |
|     |     |     | 820 |     |     |     |     | 825 |     |     |     |     | 830 |     |     |
| Leu | Ile | Leu | Asn | Ala | Tyr | Arg | Asn | Asn | Thr | Val | Val | Ser | Ser | Ile | Pro |
|     |     | 835 |     |     |     |     | 840 |     |     |     |     | 845 |     |     |     |
| Val | Tyr | Ser | Pro | Phe | Asp | Ile | Thr | Ile | Gln | Thr | Glu | Ala | Asp | Ser | Leu |
|     | 850 |     |     |     |     | 855 |     |     |     |     | 860 |     |     |     |     |
| Glu | Leu | Glu | Leu | Gln | Pro | Arg | Tyr | Gly | Phe | Ala | Thr | Val | Asn | Gly | Thr |
| 865 |     |     |     |     | 870 |     |     |     | 875 |     |     |     |     |     | 880 |
| Ala | Thr | Val | Lys | Ser | Pro | Asn | Val | Asn | Tyr | Asp | Arg | Ser | Phe | Lys | Leu |
|     |     |     |     | 885 |     |     |     |     | 890 |     |     |     |     | 895 |     |
| Pro | Ile | Asp | Leu | Gln | Asn | Ile | Thr | Thr | Gln | Val | Asn | Ala | Leu | Phe | Ala |
|     |     |     | 900 |     |     |     |     | 905 |     |     |     |     | 910 |     |     |
| Ser | Gly | Thr | Gln | Asn | Met | Leu | Ala | His | Asn | Val | Ser | Asp | His | Asp | Ile |
|     |     | 915 |     |     |     |     | 920 |     |     |     |     | 925 |     |     |     |
| Glu | Glu | Val | Val | Leu | Lys | Val | Asp | Ala | Leu | Ser | Asp | Glu | Val | Phe | Gly |
|     | 930 |     |     |     |     | 935 |     |     |     |     | 940 |     |     |     |     |

```
Asp Glu Lys Lys Ala Leu Arg Lys Leu Val Asn Gln Ala Lys Arg Leu
945             950                 955                 960

Ser Arg Ala Arg Asn Leu Leu Ile Gly Gly Ser Phe Glu Asn Trp Asp
            965                 970                 975

Ala Trp Tyr Lys Gly Arg Asn Val Val Thr Val Ser Asp His Glu Leu
        980                 985                 990

Phe Lys Ser Asp His Val Leu Pro Pro Gly Leu Ser Pro Ser
            995                 1000                1005

Tyr Ile Phe Gln Lys Val Glu Glu Ser Lys Leu Lys Pro Asn Thr Arg
        1010                1015                1020

Tyr Ile Val Ser Gly Phe Ile Ala His Gly Lys Asp Leu Glu Ile Val
1025            1030                1035                1040

Val Ser Arg Tyr Gly Gln Glu Val Gln Lys Val Val Gln Val Pro Tyr
            1045                1050                1055

Gly Glu Ala Phe Pro Leu Thr Ser Asn Gly Pro Val Cys Cys Pro Pro
            1060                1065                1070

Arg Ser Thr Ser Asn Gly Thr Leu Gly Asp Pro His Phe Phe Ser Tyr
            1075                1080                1085

Ser Ile Asp Val Gly Ala Leu Asp Leu Gln Ala Asn Pro Gly Ile Glu
        1090                1095                1100

Phe Gly Leu Arg Ile Val Asn Pro Thr Gly Met Ala Arg Val Ser Asn
1105            1110                1115                1120

Leu Glu Ile Arg Glu Asp Arg Pro Leu Ala Ala Asn Glu Ile Arg Gln
                1125                1130                1135

Val Gln Arg Val Ala Arg Asn Trp Arg Thr Glu Tyr Glu Lys Glu Arg
            1140                1145                1150

Ala Glu Val Thr Ser Leu Ile Gln Pro Val Ile Asn Arg Ile Asn Gly
            1155                1160                1165

Leu Tyr Glu Asn Gly Asn Trp Asn Gly Ser Ile Arg Ser Asp Ile Ser
            1170                1175                1180

Tyr Gln Asn Ile Asp Ala Ile Val Leu Pro Thr Leu Pro Lys Leu Arg
1185            1190                1195                1200

His Trp Phe Met Ser Asp Arg Phe Ser Glu Gln Gly Asp Ile Met Ala
                1205                1210                1215

Lys Phe Gln Gly Ala Leu Asn Arg Ala Tyr Ala Gln Leu Glu Gln Ser
            1220                1225                1230

Thr Leu Leu His Asn Gly His Phe Thr Lys Asp Ala Ala Asn Trp Thr
            1235                1240                1245

Ile Glu Gly Asp Ala His Gln Ile Thr Leu Glu Asp Gly Arg Arg Val
    1250                1255                1260

Leu Arg Leu Pro Asp Trp Ser Ser Val Ser Gln Met Ile Glu Ile
1265            1270                1275                1280

Glu Asn Phe Asn Pro Asp Lys Glu Tyr Asn Leu Val Phe His Gly Gln
                1285                1290                1295

Gly Glu Gly Thr Val Thr Leu Glu His Gly Glu Glu Thr Lys Tyr Ile
            1300                1305                1310

Glu Thr His Thr His His Phe Ala Asn Phe Thr Thr Ser Gln Arg Gln
        1315                1320                1325

Gly Leu Thr Phe Glu Ser Asn Lys Val Thr Val Thr Ile Ser Ser Glu
        1330                1335                1340

Asp Gly Glu Phe Leu Val Asp Asn Ile Ala Leu Val Glu Ala Pro Leu
1345            1350                1355                1360

Pro Thr Asp Asp Gln Asn Ser Glu Gly Asn Thr Ala Ser Ser Thr Asn
            1365                1370                1375
```

-continued

Ser Asp Thr Ser Met Asn Asn Asn Gln
1380 1385

( 2 ) INFORMATION FOR SEQ ID NO:3:

( i ) SEQUENCE CHARACTERISTICS:
( A ) LENGTH: 3867 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: PS17
( C ) INDIVIDUAL ISOLATE: PS17b ( v i i ) IMMEDIATE SOURCE:
( B ) CLONE: E. coli NM522(pMYC 1628) NRRL B-18652

( x i ) SEQUENCE DESCRIPTION: SEQ ID NO:3:

ATGGCAATTT TAAATGAATT ATATCCATCT GTACCTTATA ATGTATTGGC GTATACGCCA 60

CCCTCTTTTT TACCTGATGC GGGTACACAA GCTACACCTG CTGACTTAAC AGCTTATGAA 120

CAATTGTTGA AAAATTTAGA AAAAGGGATA AATGCTGGAA CTTATTCGAA AGCAATAGCT 180

GATGTACTTA AAGGTATTTT TATAGATGAT ACAATAAATT ATCAAACATA TGTAAATATT 240

GGTTTAAGTT TAATTACATT AGCTGTACCG GAAATTGGTA TTTTTACACC TTTCATCGGT 300

TTGTTTTTTG CTGCATTGAA TAAACATGAT GCTCCACCTC CTCCTAATGC AAAAGATATA 360

TTTGAGGCTA TGAAACCAGC GATTCAAGAG ATGATTGATA GAACTTTAAC TGCGGATGAG 420

CAAACATTTT TAAATGGGGA AATAAGTGGT TTACAAAATT TAGCAGCAAG ATACCAGTCT 480

ACAATGGATG ATATTCAAAG CCATGGAGGA TTTAATAAGG TAGATTCTGG ATTAATTAAA 540

AAGTTTACAG ATGAGGTACT ATCTTTAAAT AGTTTTTATA CAGATCGTTT ACCTGTATTT 600

ATTACAGATA ATACAGCGGA TCGAACTTTG TTAGGTCTTC CTTATTATGC TATACTTGCG 660

AGCATGCATC TTATGTTATT AAGAGATATC ATTACTAAGG GTCCGACATG GGATTCTAAA 720

ATTAATTTCA CACCAGATGC AATTGATTCC TTTAAAACCG ATATTAAAAA TAATATAAAG 780

CTTTACTCTA AAACTATTTA TGACGTATTT CAGAAGGGAC TTGCTTCATA CGGAACGCCT 840

TCTGATTTAG AGTCCTTTGC AAAAAAACAA AAATATATTG AAATTATGAC AACACATTGT 900

TTAGATTTTG CAAGATTGTT TCCTACTTTT GATCCAGATC TTTATCCAAC AGGATCAGGT 960

GATATAAGTT TACAAAAAAC ACGTAGAATT CTTTCTCCTT TTATCCCTAT ACGTACTGCA 1020

GATGGGTTAA CATTAAATAA TACTTCAATT GATACTTCAA ATTGGCCTAA TTATGAAAAT 1080

GGGAATGGCG CGTTTCCAAA CCCAAAAGAA AGAATATTAA AACAATTCAA ACTGTATCCT 1140

AGTTGGAGAG CGGCACAGTA CGGTGGGCTT TTACAACCTT ATTTATGGGC AATAGAAGTC 1200

CAAGATTCTG TAGAGACTCG TTTGTATGGG CAGCTTCCAG CTGTAGATCC ACAGGCAGGG 1260

CCTAATTATG TTTCCATAGA TTCTTCTAAT CCAATCATAC AAATAAATAT GGATACTTGG 1320

AAAACACCAC CACAAGGTGC GAGTGGGTGG AATACAAATT TAATGAGAGG AAGTGTAAGC 1380

GGGTTAAGTT TTTTACAACG AGATGGTACG AGACTTAGTG CTGGTATGGG TGGTGGTTTT 1440

GCTGATACAA TATATAGTCT CCCTGCAACT CATTATCTTT CTTATCTCTA TGGAACTCCT 1500

TATCAAACTT CTGATAACTA TTCTGGTCAC GTTGGTGCAT TGGTAGGTGT GAGTACGCCT 1560

```
CAAGAGGCTA  CTCTTCCTAA  TATTATAGGT  CAACCAGATG  AACAGGGAAA  TGTATCTACA   1620
ATGGGATTTC  CGTTTGAAAA  AGCTTCTTAT  GGAGGTACAG  TTGTTAAAGA  ATGGTTAAAT   1680
GGTGCGAATG  CGATGAAGCT  TTCTCCTGGG  CAATCTATAG  GTATTCCTAT  TACAAATGTA   1740
ACAAGTGGAG  AATATCAAAT  TCGTTGTCGT  TATGCAAGTA  ATGATAATAC  TAACGTTTTC   1800
TTTAATGTAG  ATACTGGTGG  AGCAAATCCA  ATTTTCCAAC  AGATAAACTT  TGCATCTACT   1860
GTAGATAATA  ATACGGGAGT  ACAAGGAGCA  AATGGTGTCT  ATGTAGTCAA  ATCTATTGCT   1920
ACAACTGATA  ATTCTTTTAC  AGTAAAAATT  CCTGCGAAGA  CGATTAATGT  TCATTTAACC   1980
AACCAAGGTT  CTTCTGATGT  CTTTTTAGAT  CGTATTGAGT  TTGTTCCAAT  TCTAGAATCA   2040
AATACTGTAA  CTATATTCAA  CAATTCATAT  ACTACAGGTT  CAGCAAATCT  TATACCAGCA   2100
ATAGCTCCTC  TTTGGAGTAC  TAGTTCAGAT  AAAGCCCTTA  CAGGTTCTAT  GTCAATAACA   2160
GGTCGAACTA  CCCCTAACAG  TGATGATGCT  TTGCTTCGAT  TTTTTAAAAC  TAATTATGAT   2220
ACACAAACCA  TTCCTATTCC  GGGTTCCGGA  AAAGATTTTA  CAAATACTCT  AGAAATACAA   2280
GACATAGTTT  CTATTGATAT  TTTTGTCGGA  TCTGGTCTAC  ATGGATCCGA  TGGATCTATA   2340
AAATTAGATT  TTACCAATAA  TAATAGTGGT  AGTGGTGGCT  CTCCAAAGAG  TTTCACCGAG   2400
CAAAATGATT  TAGAGAATAT  CACAACACAA  GTGAATGCTC  TATTCACATC  TAATACACAA   2460
GATGCACTTG  CAACAGATGT  GAGTGATCAT  GATATTGAAG  AAGTGGTTCT  AAAAGTAGAT   2520
GCATTATCTG  ATGAAGTGTT  TGGAAAAGAG  AAAAAAACAT  TGCGTAAATT  TGTAAATCAA   2580
GCGAAGCGCT  TAAGCAAGGC  GCGTAATCTC  CTGGTAGGAG  GCAATTTTGA  TAACTTGGAT   2640
GCTTGGTATA  GAGGAAGAAA  TGTAGTAAAC  GTATCTAATC  ACGAACTGTT  GAAGAGTGAT   2700
CATGTATTAT  TACCACCACC  AGGATTGTCT  CCATCTTATA  TTTTCCAAAA  AGTGGAGGAA   2760
TCTAAATTAA  AACGAAATAC  ACGTTATACG  GTTTCTGGAT  TTATTGCGCA  TGCAACAGAT   2820
TTAGAAATTG  TGGTTTCTCG  TTATGGGCAA  GAAATAAAGA  AAGTGGTGCA  AGTTCCTTAT   2880
GGAGAAGCAT  TCCCATTAAC  ATCAAGTGGA  CCAGTTTGTT  GTATCCCACA  TTCTACAAGT   2940
AATGGAACTT  TAGGCAATCC  ACATTTCTTT  AGTTACAGTA  TTGATGTAGG  TGCATTAGAT   3000
GTAGACACAA  ACCCTGGTAT  TGAATTCGGT  CTTCGTATTG  TAAATCCAAC  TGGAATGGCA   3060
CGCGTAAGCA  ATTTGGAAAT  TCGTGAAGAT  CGTCCATTAG  CAGCAAATGA  ATACGACAA    3120
GTACAACGTG  TCGCAAGAAA  TTGGAGAACC  GAGTATGAGA  AGAACGTGC   GGAAGTAACA   3180
AGTTTAATTC  AACCTGTTAT  CAATCGAATC  AATGGATTGT  ATGACAATGG  AAATTGGAAC   3240
GGTTCTATTC  GTTCAGATAT  TTCGTATCAG  AATATAGACG  CGATTGTATT  ACCAACGTTA   3300
CCAAAGTTAC  GCCATTGGTT  TATGTCAGAT  AGATTAGTG   AACAAGGAGA  TATCATGGCT   3360
AAATTCCAAG  GTGCATTAAA  TCGTGCGTAT  GCACAACTGG  AACAAAATAC  GCTTCTGCAT   3420
AATGGTCATT  TTACAAAAGA  TGCAGCCAAT  TGGACGGTAG  AAGGCGATGC  ACATCAGGTA   3480
GTATTAGAAG  ATGGTAAACG  TGTATTACGA  TTGCCAGATT  GGTCTTCGAG  TGTGTCTCAA   3540
ACGATTGAAA  TCGAGAATTT  TGATCCAGAT  AAAGAATATC  AATTAGTATT  TCATGGGCAA   3600
GGAGAAGGAA  CGGTTACGTT  GGAGCATGGA  GAAGAAACAA  AATATATAGA  AACGCATACA   3660
CATCATTTTG  CGAATTTTAC  AACTTCTCAA  CGTCAAGGAC  TCACGTTTGA  ATCAAATAAA   3720
GTGACAGTGA  CCATTTCTTC  AGAAGATGGA  GAATTCTTAG  TGGATAATAT  TGCGCTTGTG   3780
GAAGCTCCTC  TTCCTACAGA  TGACCAAAAT  TCTGAGGGAA  ATACGGCTTC  CAGTACGAAT   3840
AGCGATACAA  GTATGAACAA  CAATCAA                                         3867
```

(2) INFORMATION FOR SEQ ID NO:4:

(i) SEQUENCE CHARACTERISTICS:
        (A) LENGTH: 1289 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: BACILLUS THURINGIENSIS
        (C) INDIVIDUAL ISOLATE: PS17

```
Arg  Leu  Phe  Pro  Thr  Phe  Asp  Pro  Asp  Leu  Tyr  Pro  Thr  Gly  Ser  Gly
305                 310                 315                 320

Asp  Ile  Ser  Leu  Gln  Lys  Thr  Arg  Arg  Ile  Leu  Ser  Pro  Phe  Ile  Pro
                    325                 330                 335

Ile  Arg  Thr  Ala  Asp  Gly  Leu  Thr  Leu  Asn  Asn  Thr  Ser  Ile  Asp  Thr
               340                 345                 350

Ser  Asn  Trp  Pro  Asn  Tyr  Glu  Asn  Gly  Asn  Gly  Ala  Phe  Pro  Asn  Pro
          355                 360                 365

Lys  Glu  Arg  Ile  Leu  Lys  Gln  Phe  Lys  Leu  Tyr  Pro  Ser  Trp  Arg  Ala
     370                 375                 380

Ala  Gln  Tyr  Gly  Gly  Leu  Leu  Gln  Pro  Tyr  Leu  Trp  Ala  Ile  Glu  Val
385                 390                 395                      400

Gln  Asp  Ser  Val  Glu  Thr  Arg  Leu  Tyr  Gly  Gln  Leu  Pro  Ala  Val  Asp
                    405                 410                 415

Pro  Gln  Ala  Gly  Pro  Asn  Tyr  Val  Ser  Ile  Asp  Ser  Ser  Asn  Pro  Ile
               420                 425                 430

Ile  Gln  Ile  Asn  Met  Asp  Thr  Trp  Lys  Thr  Pro  Pro  Gln  Gly  Ala  Ser
          435                 440                 445

Gly  Trp  Asn  Thr  Asn  Leu  Met  Arg  Gly  Ser  Val  Ser  Gly  Leu  Ser  Phe
450                      455                 460

Leu  Gln  Arg  Asp  Gly  Thr  Arg  Leu  Ser  Ala  Gly  Met  Gly  Gly  Gly  Phe
465                 470                 475                      480

Ala  Asp  Thr  Ile  Tyr  Ser  Leu  Pro  Ala  Thr  His  Tyr  Leu  Ser  Tyr  Leu
               485                 490                 495

Tyr  Gly  Thr  Pro  Tyr  Gln  Thr  Ser  Asp  Asn  Tyr  Ser  Gly  His  Val  Gly
               500                 505                 510

Ala  Leu  Val  Gly  Val  Ser  Thr  Pro  Gln  Glu  Ala  Thr  Leu  Pro  Asn  Ile
          515                 520                 525

Ile  Gly  Gln  Pro  Asp  Glu  Gln  Gly  Asn  Val  Ser  Thr  Met  Gly  Phe  Pro
     530                 535                 540

Phe  Glu  Lys  Ala  Ser  Tyr  Gly  Gly  Thr  Val  Val  Lys  Glu  Trp  Leu  Asn
545                 550                 555                      560

Gly  Ala  Asn  Ala  Met  Lys  Leu  Ser  Pro  Gly  Gln  Ser  Ile  Gly  Ile  Pro
                    565                 570                 575

Ile  Thr  Asn  Val  Thr  Ser  Gly  Glu  Tyr  Gln  Ile  Arg  Cys  Arg  Tyr  Ala
               580                 585                 590

Ser  Asn  Asp  Asn  Thr  Asn  Val  Phe  Phe  Asn  Val  Asp  Thr  Gly  Gly  Ala
               595                 600                 605

Asn  Pro  Ile  Phe  Gln  Gln  Ile  Asn  Phe  Ala  Ser  Thr  Val  Asp  Asn  Asn
     610                 615                 620

Thr  Gly  Val  Gln  Gly  Ala  Asn  Gly  Val  Tyr  Val  Val  Lys  Ser  Ile  Ala
625                 630                 635                      640

Thr  Thr  Asp  Asn  Ser  Phe  Thr  Val  Lys  Ile  Pro  Ala  Lys  Thr  Ile  Asn
               645                 650                 655

Val  His  Leu  Thr  Asn  Gln  Gly  Ser  Ser  Asp  Val  Phe  Leu  Asp  Arg  Ile
               660                 665                 670

Glu  Phe  Val  Pro  Ile  Leu  Glu  Ser  Asn  Thr  Val  Thr  Ile  Phe  Asn  Asn
          675                 680                 685

Ser  Tyr  Thr  Thr  Gly  Ser  Ala  Asn  Leu  Ile  Pro  Ala  Ile  Ala  Pro  Leu
          690                 695                 700

Trp  Ser  Thr  Ser  Ser  Asp  Lys  Ala  Leu  Thr  Gly  Ser  Met  Ser  Ile  Thr
705                 710                 715                      720

Gly  Arg  Thr  Thr  Pro  Asn  Ser  Asp  Asp  Ala  Leu  Leu  Arg  Phe  Phe  Lys
                    725                 730                 735
```

```
Thr  Asn  Tyr  Asp  Thr  Gln  Thr  Ile  Pro  Ile  Pro  Gly  Ser  Gly  Lys  Asp
               740                      745                     750

Phe  Thr  Asn  Thr  Leu  Glu  Ile  Gln  Asp  Ile  Val  Ser  Ile  Asp  Ile  Phe
          755                      760                     765

Val  Gly  Ser  Gly  Leu  His  Gly  Ser  Asp  Gly  Ser  Ile  Lys  Leu  Asp  Phe
     770                      775                     780

Thr  Asn  Asn  Asn  Ser  Gly  Ser  Gly  Gly  Ser  Pro  Lys  Ser  Phe  Thr  Glu
785                      790                     795                          800

Gln  Asn  Asp  Leu  Glu  Asn  Ile  Thr  Thr  Gln  Val  Asn  Ala  Leu  Phe  Thr
                    805                      810                     815

Ser  Asn  Thr  Gln  Asp  Ala  Leu  Ala  Thr  Asp  Val  Ser  Asp  His  Asp  Ile
               820                      825                     830

Glu  Glu  Val  Val  Leu  Lys  Val  Asp  Ala  Leu  Ser  Asp  Glu  Val  Phe  Gly
               835                      840                     845

Lys  Glu  Lys  Lys  Thr  Leu  Arg  Lys  Phe  Val  Asn  Gln  Ala  Lys  Arg  Leu
850                      855                     860

Ser  Lys  Ala  Arg  Asn  Leu  Leu  Val  Gly  Gly  Asn  Phe  Asp  Asn  Leu  Asp
865                      870                     875                          880

Ala  Trp  Tyr  Arg  Gly  Arg  Asn  Val  Val  Asn  Val  Ser  Asn  His  Glu  Leu
                    885                      890                     895

Leu  Lys  Ser  Asp  His  Val  Leu  Leu  Pro  Pro  Gly  Leu  Ser  Pro  Ser
               900                      905                     910

Tyr  Ile  Phe  Gln  Lys  Val  Glu  Glu  Ser  Lys  Leu  Lys  Arg  Asn  Thr  Arg
          915                      920                     925

Tyr  Thr  Val  Ser  Gly  Phe  Ile  Ala  His  Ala  Thr  Asp  Leu  Glu  Ile  Val
     930                      935                     940

Val  Ser  Arg  Tyr  Gly  Gln  Glu  Ile  Lys  Lys  Val  Val  Gln  Val  Pro  Tyr
945                      950                     955                          960

Gly  Glu  Ala  Phe  Pro  Leu  Thr  Ser  Ser  Gly  Pro  Val  Cys  Cys  Ile  Pro
                    965                      970                     975

His  Ser  Thr  Ser  Asn  Gly  Thr  Leu  Gly  Asn  Pro  His  Phe  Phe  Ser  Tyr
               980                      985                     990

Ser  Ile  Asp  Val  Gly  Ala  Leu  Asp  Val  Asp  Thr  Asn  Pro  Gly  Ile  Glu
          995                      1000                    1005

Phe  Gly  Leu  Arg  Ile  Val  Asn  Pro  Thr  Gly  Met  Ala  Arg  Val  Ser  Asn
     1010                     1015                    1020

Leu  Glu  Ile  Arg  Glu  Asp  Arg  Pro  Leu  Ala  Ala  Asn  Glu  Ile  Arg  Gln
1025                     1030                    1035                         1040

Val  Gln  Arg  Val  Ala  Arg  Asn  Trp  Arg  Thr  Glu  Tyr  Glu  Lys  Glu  Arg
               1045                     1050                    1055

Ala  Glu  Val  Thr  Ser  Leu  Ile  Gln  Pro  Val  Ile  Asn  Arg  Ile  Asn  Gly
               1060                     1065                    1070

Leu  Tyr  Asp  Asn  Gly  Asn  Trp  Asn  Gly  Ser  Ile  Arg  Ser  Asp  Ile  Ser
          1075                     1080                    1085

Tyr  Gln  Asn  Ile  Asp  Ala  Ile  Val  Leu  Pro  Thr  Leu  Pro  Lys  Leu  Arg
     1090                     1095                    1100

His  Trp  Phe  Met  Ser  Asp  Arg  Phe  Ser  Glu  Gln  Gly  Asp  Ile  Met  Ala
1105                     1110                    1115                         1120

Lys  Phe  Gln  Gly  Ala  Leu  Asn  Arg  Ala  Tyr  Ala  Gln  Leu  Glu  Gln  Asn
                    1125                     1130                    1135

Thr  Leu  Leu  His  Asn  Gly  His  Phe  Thr  Lys  Asp  Ala  Ala  Asn  Trp  Thr
               1140                     1145                    1150

Val  Glu  Gly  Asp  Ala  His  Gln  Val  Val  Leu  Glu  Asp  Gly  Lys  Arg  Val
```

```
                        1155                      1160                           1165
       Leu  Arg  Leu  Pro  Asp  Trp  Ser  Ser  Ser  Val  Ser  Gln  Thr  Ile  Glu  Ile
                 1170                      1175                      1180

Glu  Asn  Phe  Asp  Pro  Asp  Lys  Glu  Tyr  Gln  Leu  Val  Phe  His  Gly  Gln
       1185                     1190                      1195                     1200

Gly  Glu  Gly  Thr  Val  Thr  Leu  Glu  His  Gly  Glu  Glu  Thr  Lys  Tyr  Ile
                           1205                      1210                     1215

Glu  Thr  His  Thr  His  His  Phe  Ala  Asn  Phe  Thr  Thr  Ser  Gln  Arg  Gln
                      1220                     1225                      1230

Gly  Leu  Thr  Phe  Glu  Ser  Asn  Lys  Val  Thr  Val  Thr  Ile  Ser  Ser  Glu
                 1235                     1240                      1245

Asp  Gly  Glu  Phe  Leu  Val  Asp  Asn  Ile  Ala  Leu  Val  Glu  Ala  Pro  Leu
       1250                      1255                      1260

Pro  Thr  Asp  Asp  Gln  Asn  Ser  Glu  Gly  Asn  Thr  Ala  Ser  Ser  Thr  Asn
       1265                     1270                      1275                     1280

Ser  Asp  Thr  Ser  Met  Asn  Asn  Asn  Gln
                           1285
```

( 2 ) INFORMATION FOR SEQ ID NO:5 (PS33F2):

( i ) SEQUENCE CHARACTERISTICS:
    ( A ) LENGTH: 3771 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Bacillus thuringiensis
    ( C ) INDIVIDUAL ISOLATE: 33f2

( v i i ) IMMEDIATE SOURCE:
    ( B ) CLONE: E. coli NM522(pMYC 2316) B-18785

( i x ) FEATURE:
( A ) NAME/KEY: misc_feature
( B ) LOCATION: 4..24
( D ) OTHER INFORMATION: /function=oligonucleotide
hybridization probe"
/ product= GCA/T ACA/T TTA AAT GAA GTA/T TAT"
/ standard_name= probe a"
/ note= Probe A"

( i x ) FEATURE:
( A ) NAME/KEY: misc_feature
( B ) LOCATION: 13..33
( D ) OTHER INFORMATION: /function=oligonucleotide
hybridization probe"
/ product= AAT GAA GTA/T TAT CCA/T GTA/T AAT"
/ standard_name= Probe B"
/ label= probe-b
/ note= probe b"

( x i ) SEQUENCE DESCRIPTION: SEQ ID NO:5:

ATGGCTACAC TTAATGAAGT ATATCCTGTG AATTATAATG TATTATCTTC TGATGCTTTT 60

CAACAATTAG ATACAACAGG TTTTAAAAGT AAATATGATG AAATGATAAA AGCATTCGAA 120

AAAAAATGGA AAAAAGGGGC AAAAGGAAAA GACCTTTTAG ATGTTGCATG GACTTATATA 180

ACTACAGGAG AAATTGACCC TTTAAATGTA ATTAAAGGTG TTTTATCTGTATTAACTTTA 240

ATTCCTGAAG TTGGTACTGT GGCCTCTGCA GCAAGTACTA TTGTAAGTTT TATTTGGCCT 300

AAAATATTTG GAGATAAACC AAATGCAAAA AATATATTTG AAGAGCTCAA GCCTCAAATT 360

```
GAAGCATTAA TTCAACAAGA TATAACAAAC TATCAAGATG CAATTAATCA AAAAAAATTT    420
GACAGTCTTC AGAAAACAAT TAATCTATAT ACAGTAGCTA TAGATAACAA TGATTACGTA    480
ACAGCAAAAA CGCAACTCGA AAATCTAAAT TCTATACTTA CCTCAGATAT CTCCATATTT    540
ATTCCAGAAG GATATGAAAC TGGAGGTTTA CCTTATTATG CTATGGTTGC TAATGCTCAT    600
ATATTATTGT TAAGAGACGC TATAGTTAAT GCAGAGAAAT TAGGCTTTAG TGATAAAGAA    660
GTAGACACAC ATAAAAAATA TATCAAAATG ACAATACACA ATCATACTGA AGCAGTAATA    720
AAAGCATTCT TAAATGGACT TGACAAATTT AAGAGTTTAG ATGTAAATAG CTATAATAAA    780
AAAGCAAATT ATATTAAAGG TATGACAGAA ATGGTTCTTG ATCTAGTTGC TCTATGGCCA    840
ACTTTCGATC CAGATCATTA TCAAAAGAA GTAGAAATTG AATTACAAG AACTATTTCT    900
TCTCCAATTT ACCAACCTGT ACCTAAAAAC ATGCAAAATA CCTCTAGCTC TATTGTACCT    960
AGCGATCTAT TTCACTATCA AGGAGATCTT GTAAAATTAG AATTTCTAC AAGAACGGAC   1020
AACGATGGTC TTGCAAAAAT TTTTACTGGT ATTCGAAACA CATTCTACAA ATCGCCTAAT   1080
ACTCATGAAA CATACCATGT AGATTTAGT TATAATACCC AATCTAGTGG TAATATTTCA   1140
AGAGGCTCTT CAAATCCGAT TCCAATTGAT CTTAATAATC CCATTATTTC AACTTGTATT   1200
AGAAATTCAT TTTATAAGGC AATAGCGGGA TCTTCTGTTT TAGTTAATTT TAAAGATGGC   1260
ACTCAAGGGT ATGCATTTGC CCAAGCACCA ACAGGAGGTG CCTGGGACCA TTCTTTTATT   1320
GAATCTGATG GTGCCCCAGA AGGGCATAAA TTAAACTATA TTTATACTTC TCCAGGTGAT   1380
ACATTAAGAG ATTTCATCAA TGTATATACT CTTATAAGTA CTCCAACTAT AAATGAACTA   1440
TCAACAGAAA AAATCAAAGG CTTTCCTGCG GAAAAAGGAT ATATCAAAAA TCAAGGGATC   1500
ATGAAATATT ACGGTAAACC AGAATATATT AATGGAGCTC AACCAGTTAA TCTGGAAAAC   1560
CAGCAAACAT TAATATTCGA ATTTCATGCT TCAAAAACAG CTCAATATAC CATTCGTATA   1620
CGTTATGCCA GTACCCAAGG AACAAAAGGT TATTTTCGTT TAGATAATCA GGAACTGCAA   1680
ACGCTTAATA TACCTACTTC ACACAACGGT TATGTAACCG GTAATATTGG TGAAAATTAT   1740
GATTTATATA CAATAGGTTC ATATACAATT ACAGAAGGTA ACCATACTCT TCAAATCCAA   1800
CATAATGATA AAAATGGAAT GGTTTTAGAT CGTATTGAAT TTGTTCCTAA AGATTCACTT   1860
CAAGATTCAC CTCAAGATTC ACCTCCAGAA GTTCACGAAT CAACAATTAT TTTTGATAAA   1920
TCATCTCCAA CTATATGGTC TTCTAACAAA CACTCATATA GCCATATACA TTAGAAGGA   1980
TCATATACAA GTCAGGGAAG TTATCCACAC AATTTATTAA TTAATTTATT TCATCCTACA   2040
GACCCTAACA GAAATCATAC TATTCATGTT AACAATGGTG ATATGAATGT TGATTATGGA   2100
AAAGATTCTG TAGCCGATGG GTTAAATTTT AATAAAATAA CTGCTACGAT ACCAAGTGAT   2160
GCTTGGTATA GCGGTACTAT TACTTCTATG CACTTATTTA ATGATAATAA TTTTAAAACA   2220
ATAACTCCTA AATTTGAACT TTCTAATGAA TTAGAAAACA TCACAACTCA AGTAAATGCT   2280
TTATTCGCAT CTAGTGCACA AGATACTCTC GCAAGTAATG TAAGTGATTA CTGGATTGAA   2340
CAGGTCGTTA TGAAAGTCGA TGCCTTATCA GATGAAGTAT TTGGAAAAGA GAAAAAGCA   2400
TTACGTAAAT TGGTAAATCA AGCAAAACGT CTCAGTAAAA TACGAAATCT TCTCATAGGT   2460
GGTAATTTTG ACAATTTAGT CGCTTGGTAT ATGGGAAAAG ATGTAGTAAA AGAATCGGAT   2520
CATGAATTAT TTAAAAGTGA TCATGTCTTA CTACCTCCCC CAACATTCCA TCCTTCTTAT   2580
ATTTTCCAAA AGGTGGAAGA ATCAAAACTA AAACCAAATA CACGTTATAC TATTTCTGGT   2640
TTTATCGCAC ATGGAGAAGA TGTAGAGCTT GTTGTCTCTC GTTATGGGCA AGAAATACAA   2700
AAAGTGATGC AAGTGCCATA TGAAGAAGCA CTTCCTCTTA CATCTGAATC TAATTCTAGT   2760
```

-continued

```
TGTTGTGTTC CAAATTTAAA TATAAATGAA ACACTAGCTG ATCCACATTT CTTTAGTTAT   2820

AGCATCGATG TTGGTTCTCT GGAAATGGAA GCGAATCCTG GTATTGAATT TGGTCTCCGT   2880

ATTGTCAAAC CAACAGGTAT GGCACGTGTA AGTAATTTAG AAATTCGAGA AGACCGTCCA   2940

TTAACAGCAA AAGAAATTCG TCAAGTACAA CGTGCAGCAA GAGATTGGAA ACAAAACTAT   3000

GAACAAGAAC GAACAGAGAT CACAGCTATA ATTCAACCTG TTCTTAATCA AATTAATGCG   3060

TTATACGAAA ATGAAGATTG GAATGGTTCT ATTCGTTCAA ATGTTTCCTA TCATGATCTA   3120

GAGCAAATTA TGCTTCCTAC TTTATTAAAA ACTGAGGAAA TAAATTGTAA TTATGATCAT   3180

CCAGCTTTTT TATTAAAAGT ATATCATTGG TTTATGACAG ATCGTATAGG AGAACATGGT   3240

ACTATTTTAG CACGTTTCCA AGAAGCATTA GATCGTGCAT ATACACAATT AGAAAGTCGT   3300

AATCTCCTGC ATAACGGTCA TTTTACAACT GATACAGCGA ATTGGACAAT AGAAGGAGAT   3360

GCCCATCATA CAATCTTAGA AGATGGTAGA CGTGTGTTAC GTTTACCAGA TTGGTCTTCT   3420

AATGCAACTC AAACAATTGA AATTGAAGAT TTTGACTTAG ATCAAGAATA CCAATTGCTC   3480

ATTCATGCAA AAGGAAAAGG TTCCATTACT TTACAACATG GAGAAGAAAA CGAATATGTG   3540

GAAACACATA CTCATCATAC AAATGATTTT ATAACATCCC AAAATATTCC TTTCACTTTT   3600

AAAGGAAATC AAATTGAAGT CCATATTACT TCAGAAGATG GAGAGTTTTT AATCGATCAC   3660

ATTACAGTAA TAGAAGTTTC TAAAACAGAC ACAAATACAA ATATTATTGA AAATTCACCA   3720

ATCAATACAA GTATGAATAG TAATGTAAGA GTAGATATAC CAAGAAGTCT C            3771
```

( 2 ) INFORMATION FOR SEQ ID NO:6 (PS33F2):

( i ) SEQUENCE CHARACTERISTICS:
( A ) LENGTH: 1257 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( C ) INDIVIDUAL ISOLATE: PS33F2

( v i i ) IMMEDIATE SOURCE:
( B ) CLONE: E. coli NM522(pMYC 2316) B-18785

( i x ) FEATURE:
( A ) NAME/KEY: Protein
( B ) LOCATION: 1..1257

( x i ) SEQUENCE DESCRIPTION: SEQ ID NO:6:

```
Met Ala Thr Leu Asn Glu Val Tyr Pro Val Asn Tyr Asn Val Leu Ser
1               5                   10                  15

Ser Asp Ala Phe Gln Gln Leu Asp Thr Thr Gly Phe Lys Ser Lys Tyr
            20                  25                  30

Asp Glu Met Ile Lys Ala Phe Glu Lys Lys Trp Lys Lys Gly Ala Lys
        35                  40                  45

Gly Lys Asp Leu Leu Asp Val Ala Trp Thr Tyr Ile Thr Thr Gly Glu
    50                  55                  60

Ile Asp Pro Leu Asn Val Ile Lys Gly Val Leu Ser Val Leu Thr Leu
65                  70                  75                  80

Ile Pro Glu Val Gly Thr Val Ala Ser Ala Ala Ser Thr Ile Val Ser
                85                  90                  95
```

```
Phe  Ile  Trp  Pro  Lys  Ile  Phe  Gly  Asp  Lys  Pro  Asn  Ala  Lys  Asn  Ile
               100                 105                 110

Phe  Glu  Glu  Leu  Lys  Pro  Gln  Ile  Glu  Ala  Leu  Ile  Gln  Gln  Asp  Ile
          115                 120                 125

Thr  Asn  Tyr  Gln  Asp  Ala  Ile  Asn  Gln  Lys  Lys  Phe  Asp  Ser  Leu  Gln
     130                 135                 140

Lys  Thr  Ile  Asn  Leu  Tyr  Thr  Val  Ala  Ile  Asp  Asn  Asn  Asp  Tyr  Val
145                 150                 155                                 160

Thr  Ala  Lys  Thr  Gln  Leu  Glu  Asn  Leu  Asn  Ser  Ile  Leu  Thr  Ser  Asp
               165                 170                      175

Ile  Ser  Ile  Phe  Ile  Pro  Glu  Gly  Tyr  Glu  Thr  Gly  Gly  Leu  Pro  Tyr
               180                 185                      190

Tyr  Ala  Met  Val  Ala  Asn  Ala  His  Ile  Leu  Leu  Leu  Arg  Asp  Ala  Ile
          195                 200                 205

Val  Asn  Ala  Glu  Lys  Leu  Gly  Phe  Ser  Asp  Lys  Glu  Val  Asp  Thr  His
     210                 215                 220

Lys  Lys  Tyr  Ile  Lys  Met  Thr  Ile  His  Asn  His  Thr  Glu  Ala  Val  Ile
225                 230                 235                                 240

Lys  Ala  Phe  Leu  Asn  Gly  Leu  Asp  Lys  Phe  Lys  Ser  Leu  Asp  Val  Asn
               245                 250                      255

Ser  Tyr  Asn  Lys  Lys  Ala  Asn  Tyr  Ile  Lys  Gly  Met  Thr  Glu  Met  Val
               260                 265                      270

Leu  Asp  Leu  Val  Ala  Leu  Trp  Pro  Thr  Phe  Asp  Pro  Asp  His  Tyr  Gln
          275                 280                 285

Lys  Glu  Val  Glu  Ile  Glu  Phe  Thr  Arg  Thr  Ile  Ser  Ser  Pro  Ile  Tyr
     290                 295                 300

Gln  Pro  Val  Pro  Lys  Asn  Met  Gln  Asn  Thr  Ser  Ser  Ile  Val  Pro
305                 310                 315                            320

Ser  Asp  Leu  Phe  His  Tyr  Gln  Gly  Asp  Leu  Val  Lys  Leu  Glu  Phe  Ser
               325                 330                      335

Thr  Arg  Thr  Asp  Asn  Asp  Gly  Leu  Ala  Lys  Ile  Phe  Thr  Gly  Ile  Arg
               340                 345                      350

Asn  Thr  Phe  Tyr  Lys  Ser  Pro  Asn  Thr  His  Glu  Thr  Tyr  His  Val  Asp
          355                 360                 365

Phe  Ser  Tyr  Asn  Thr  Gln  Ser  Ser  Gly  Asn  Ile  Ser  Arg  Gly  Ser  Ser
     370                 375                 380

Asn  Pro  Ile  Pro  Ile  Asp  Leu  Asn  Asn  Pro  Ile  Ile  Ser  Thr  Cys  Ile
385                 390                 395                                 400

Arg  Asn  Ser  Phe  Tyr  Lys  Ala  Ile  Ala  Gly  Ser  Ser  Val  Leu  Val  Asn
               405                 410                      415

Phe  Lys  Asp  Gly  Thr  Gln  Gly  Tyr  Ala  Phe  Ala  Gln  Ala  Pro  Thr  Gly
               420                 425                      430

Gly  Ala  Trp  Asp  His  Ser  Phe  Ile  Glu  Ser  Asp  Gly  Ala  Pro  Glu  Gly
          435                 440                 445

His  Lys  Leu  Asn  Tyr  Ile  Tyr  Thr  Ser  Pro  Gly  Asp  Thr  Leu  Arg  Asp
     450                 455                 460

Phe  Ile  Asn  Val  Tyr  Thr  Leu  Ile  Ser  Thr  Pro  Thr  Ile  Asn  Glu  Leu
465                 470                 475                                 480

Ser  Thr  Glu  Lys  Ile  Lys  Gly  Phe  Pro  Ala  Glu  Lys  Gly  Tyr  Ile  Lys
               485                 490                      495

Asn  Gln  Gly  Ile  Met  Lys  Tyr  Tyr  Gly  Lys  Pro  Glu  Tyr  Ile  Asn  Gly
               500                 505                      510

Ala  Gln  Pro  Val  Asn  Leu  Glu  Asn  Gln  Gln  Thr  Leu  Ile  Phe  Glu  Phe
```

-continued

|   |     | 515 |     |     |     | 520 |     |     |     | 525 |     |     |     |     |
|---|-----|-----|-----|-----|-----|-----|-----|-----|-----|-----|-----|-----|-----|-----|

His Ala Ser Lys Thr Ala Gln Tyr Thr Ile Arg Ile Arg Tyr Ala Ser
                530                 535                 540

Thr Gln Gly Thr Lys Gly Tyr Phe Arg Leu Asp Asn Gln Glu Leu Gln
545                 550                 555                 560

Thr Leu Asn Ile Pro Thr Ser His Asn Gly Tyr Val Thr Gly Asn Ile
                    565                 570                 575

Gly Glu Asn Tyr Asp Leu Tyr Thr Ile Gly Ser Tyr Thr Ile Thr Glu
                580                 585                 590

Gly Asn His Thr Leu Gln Ile Gln His Asn Asp Lys Asn Gly Met Val
            595                 600                 605

Leu Asp Arg Ile Glu Phe Val Pro Lys Asp Ser Leu Gln Asp Ser Pro
            610                 615                 620

Gln Asp Ser Pro Pro Glu Val His Glu Ser Thr Ile Ile Phe Asp Lys
625                 630                 635                 640

Ser Ser Pro Thr Ile Trp Ser Ser Asn Lys His Ser Tyr Ser His Ile
                    645                 650                 655

His Leu Glu Gly Ser Tyr Thr Ser Gln Gly Ser Tyr Pro His Asn Leu
                660                 665                 670

Leu Ile Asn Leu Phe His Pro Thr Asp Pro Asn Arg Asn His Thr Ile
            675                 680                 685

His Val Asn Asn Gly Asp Met Asn Val Asp Tyr Gly Lys Asp Ser Val
            690                 695                 700

Ala Asp Gly Leu Asn Phe Asn Lys Ile Thr Ala Thr Ile Pro Ser Asp
705                 710                 715                 720

Ala Trp Tyr Ser Gly Thr Ile Thr Ser Met His Leu Phe Asn Asp Asn
                    725                 730                 735

Asn Phe Lys Thr Ile Thr Pro Lys Phe Glu Leu Ser Asn Glu Leu Glu
                740                 745                 750

Asn Ile Thr Thr Gln Val Asn Ala Leu Phe Ala Ser Ser Ala Gln Asp
            755                 760                 765

Thr Leu Ala Ser Asn Val Ser Asp Tyr Trp Ile Glu Gln Val Val Met
770                 775                 780

Lys Val Asp Ala Leu Ser Asp Glu Val Phe Gly Lys Glu Lys Lys Ala
785                 790                 795                 800

Leu Arg Lys Leu Val Asn Gln Ala Lys Arg Leu Ser Lys Ile Arg Asn
                    805                 810                 815

Leu Leu Ile Gly Gly Asn Phe Asp Asn Leu Val Ala Trp Tyr Met Gly
                820                 825                 830

Lys Asp Val Val Lys Glu Ser Asp His Glu Leu Phe Lys Ser Asp His
            835                 840                 845

Val Leu Leu Pro Pro Pro Thr Phe His Pro Ser Tyr Ile Phe Gln Lys
850                 855                 860

Val Glu Glu Ser Lys Leu Lys Pro Asn Thr Arg Tyr Thr Ile Ser Gly
865                 870                 875                 880

Phe Ile Ala His Gly Glu Asp Val Glu Leu Val Val Ser Arg Tyr Gly
                    885                 890                 895

Gln Glu Ile Gln Lys Val Met Gln Val Pro Tyr Glu Glu Ala Leu Pro
                900                 905                 910

Leu Thr Ser Glu Ser Asn Ser Ser Cys Cys Val Pro Asn Leu Asn Ile
            915                 920                 925

Asn Glu Thr Leu Ala Asp Pro His Phe Phe Ser Tyr Ser Ile Asp Val
930                 935                 940

| | | | | | | | | | | | | | | |
|---|---|---|---|---|---|---|---|---|---|---|---|---|---|---|
| Gly | Ser | Leu | Glu | Met | Glu | Ala | Asn | Pro | Gly | Ile | Glu | Phe | Gly | Leu | Arg |
| 945 | | | | | 950 | | | | 955 | | | | | 960 |
| Ile | Val | Lys | Pro | Thr | Gly | Met | Ala | Arg | Val | Ser | Asn | Leu | Glu | Ile | Arg |
| | | | | 965 | | | | | 970 | | | | | 975 |
| Glu | Asp | Arg | Pro | Leu | Thr | Ala | Lys | Glu | Ile | Arg | Gln | Val | Gln | Arg | Ala |
| | | | 980 | | | | | 985 | | | | | 990 | | |
| Ala | Arg | Asp | Trp | Lys | Gln | Asn | Tyr | Glu | Gln | Glu | Arg | Thr | Glu | Ile | Thr |
| | | 995 | | | | | | 1000 | | | | | 1005 | | |
| Ala | Ile | Ile | Gln | Pro | Val | Leu | Asn | Gln | Ile | Asn | Ala | Leu | Tyr | Glu | Asn |
| | | 1010 | | | | | 1015 | | | | | 1020 | | | |
| Glu | Asp | Trp | Asn | Gly | Ser | Ile | Arg | Ser | Asn | Val | Ser | Tyr | His | Asp | Leu |
| 1025 | | | | | 1030 | | | | | 1035 | | | | | 1040 |
| Glu | Gln | Ile | Met | Leu | Pro | Thr | Leu | Leu | Lys | Thr | Glu | Glu | Ile | Asn | Cys |
| | | | | 1045 | | | | | 1050 | | | | | 1055 | |
| Asn | Tyr | Asp | His | Pro | Ala | Phe | Leu | Leu | Lys | Val | Tyr | His | Trp | Phe | Met |
| | | | 1060 | | | | | 1065 | | | | | 1070 | | |
| Thr | Asp | Arg | Ile | Gly | Glu | His | Gly | Thr | Ile | Leu | Ala | Arg | Phe | Gln | Glu |
| | | | 1075 | | | | 1080 | | | | | 1085 | | | |
| Ala | Leu | Asp | Arg | Ala | Tyr | Thr | Gln | Leu | Glu | Ser | Arg | Asn | Leu | Leu | His |
| | | 1090 | | | | | 1095 | | | | | 1100 | | | |
| Asn | Gly | His | Phe | Thr | Thr | Asp | Thr | Ala | Asn | Trp | Thr | Ile | Glu | Gly | Asp |
| 1105 | | | | | 1110 | | | | | 1115 | | | | | 1120 |
| Ala | His | His | Thr | Ile | Leu | Glu | Asp | Gly | Arg | Arg | Val | Leu | Arg | Leu | Pro |
| | | | | 1125 | | | | | 1130 | | | | | 1135 | |
| Asp | Trp | Ser | Ser | Asn | Ala | Thr | Gln | Thr | Ile | Glu | Ile | Glu | Asp | Phe | Asp |
| | | | | 1140 | | | | | 1145 | | | | | 1150 | |
| Leu | Asp | Gln | Glu | Tyr | Gln | Leu | Leu | Ile | His | Ala | Lys | Gly | Lys | Gly | Ser |
| | | | | 1155 | | | | | 1160 | | | | | 1165 | |
| Ile | Thr | Leu | Gln | His | Gly | Glu | Glu | Asn | Glu | Tyr | Val | Glu | Thr | His | Thr |
| | | | | 1170 | | | | | 1175 | | | | | 1180 | |
| His | His | Thr | Asn | Asp | Phe | Ile | Thr | Ser | Gln | Asn | Ile | Pro | Phe | Thr | Phe |
| 1185 | | | | | 1190 | | | | | 1195 | | | | | 1200 |
| Lys | Gly | Asn | Gln | Ile | Glu | Val | His | Ile | Thr | Ser | Glu | Asp | Gly | Glu | Phe |
| | | | | 1205 | | | | | 1210 | | | | | 1215 | |
| Leu | Ile | Asp | His | Ile | Thr | Val | Ile | Glu | Val | Ser | Lys | Thr | Asp | Thr | Asn |
| | | | 1220 | | | | | 1225 | | | | | 1230 | | |
| Thr | Asn | Ile | Ile | Glu | Asn | Ser | Pro | Ile | Asn | Thr | Ser | Met | Asn | Ser | Asn |
| | | | | 1235 | | | | 1240 | | | | | 1245 | | |
| Val | Arg | Val | Asp | Ile | Pro | Arg | Ser | Leu |
| | 1250 | | | | | 1255 | | |

( 2 ) INFORMATION FOR SEQ ID NO:7 (PS52A1):

( i ) SEQUENCE CHARACTERISTICS:
      ( A ) LENGTH: 1425 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: BACILLUS THURINGIENSIS
      ( C ) INDIVIDUAL ISOLATE: PS52A1

( v i i ) IMMEDIATE SOURCE:

(B) CLONE: E. coli NM522(pMYC 2321) B-18770

(ix) FEATURE:
    (A) NAME/KEY: mat_peptide
    (B) LOCATION: 1..1425
    (D) OTHER INFORMATION: /product= "OPEN READING FRAME OF MATURE PROTEIN"

(xi) SEQUENCE DESCRIPTION: SEQ ID NO:7:

| | | | | | |
|---|---|---|---|---|---|
| ATGATTATTG | ATAGTAAAAC | GACTTTACCT | AGACATTCAC | TTATTCATAC | AATTAAATTA | 60 |
| AATTCTAATA | AGAAATATGG | TCCTGGTGAT | ATGACTAATG | GAAATCAATT | TATTATTTCA | 120 |
| AAACAAGAAT | GGGCTACGAT | TGGAGCATAT | ATTCAGACTG | GATTAGGTTT | ACCAGTAAAT | 180 |
| GAACAACAAT | TAAGAACACA | TGTTAATTTA | AGTCAGGATA | TATCAATACC | TAGTGATTTT | 240 |
| TCTCAATTAT | ATGATGTTTA | TTGTTCTGAT | AAAACTTCAG | CAGAATGGTG | GAATAAAAAT | 300 |
| TTATATCCTT | TAATTATTAA | ATCTGCTAAT | GATATTGCTT | CATATGGTTT | TAAAGTTGCT | 360 |
| GGTGATCCTT | CTATTAAGAA | AGATGGATAT | TTTAAAAAAT | TGCAAGATGA | ATTAGATAAT | 420 |
| ATTGTTGATA | ATAATTCCGA | TGATGATGCA | ATAGCTAAAG | CTATTAAAGA | TTTTAAAGCG | 480 |
| CGATGTGGTA | TTTTAATTAA | AGAAGCTAAA | CAATATGAAG | AAGCTGCAAA | AAATATTGTA | 540 |
| ACATCTTTAG | ATCAATTTTT | ACATGGTGAT | CAGAAAAAAT | TAGAAGGTGT | TATCAATATT | 600 |
| CAAAAACGTT | TAAAAGAAGT | TCAAACAGCT | CTTAATCAAG | CCCATGGGGA | AAGTAGTCCA | 660 |
| GCTCATAAAG | AGTTATTAGA | AAAAGTAAAA | AATTTAAAAA | CAACATTAGA | AAGGACTATT | 720 |
| AAAGCTGAAC | AAGATTTAGA | GAAAAAAGTA | GAATATAGTT | TTCTATTAGG | ACCATTGTTA | 780 |
| GGATTTGTTG | TTTATGAAAT | TCTTGAAAAT | ACTGCTGTTC | AGCATATAAA | AAATCAAATT | 840 |
| GATGAGATAA | AGAAACAATT | AGATTCTGCT | CAGCATGATT | TGGATAGAGA | TGTTAAAATT | 900 |
| ATAGGAATGT | TAAATAGTAT | TAATACAGAT | ATTGATAATT | TATATAGTCA | AGGACAAGAA | 960 |
| GCAATTAAAG | TTTTCCAAAA | GTTACAAGGT | ATTTGGGCTA | CTATTGGAGC | TCAAATAGAA | 1020 |
| AATCTTAGAA | CAACGTCGTT | ACAAGAAGTT | CAAGATTCTG | ATGATGCTGA | TGAGATACAA | 1080 |
| ATTGAACTTG | AGGACGCTTC | TGATGCTTGG | TTAGTTGTGG | CTCAAGAAGC | TCGTGATTTT | 1140 |
| ACACTAAATG | CTTATTCAAC | TAATAGTAGA | CAAAATTTAC | CGATTAATGT | TATATCAGAT | 1200 |
| TCATGTAATT | GTTCAACAAC | AAATATGACA | TCAAATCAAT | ACAGTAATCC | AACAACAAAT | 1260 |
| ATGACATCAA | ATCAATATAT | GATTTCACAT | GAATATACAA | GTTACCAAA | TAATTTTATG | 1320 |
| TTATCAAGAA | ATAGTAATTT | AGAATATAAA | TGTCCTGAAA | ATAATTTTAT | GATATATTGG | 1380 |
| TATAATAATT | CGGATTGGTA | TAATAATTCG | GATTGGTATA | ATAAT | | 1425 |

(2) INFORMATION FOR SEQ ID NO:8 (PS52A1):

(i) SEQUENCE CHARACTERISTICS:
        (A) LENGTH: 475 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (v) ORIGINAL SOURCE:
        (A) ORGANISM: BACILLUS THURINGIENSIS
        (C) INDIVIDUAL ISOLATE: PS52A1

(vii) IMMEDIATE SOURCE:
        (B) CLONE: E. coli NM522(pMYC 2321) B-18770

( i x ) FEATURE:
 ( A ) NAME/KEY: Protein
 ( B ) LOCATION: 1..475

( x i ) SEQUENCE DESCRIPTION: SEQ ID NO:8:

| Met | Ile | Ile | Asp | Ser | Lys | Thr | Thr | Leu | Pro | Arg | His | Ser | Leu | Ile | His |
|---|---|---|---|---|---|---|---|---|---|---|---|---|---|---|---|
| 1 | | | | 5 | | | | | 10 | | | | | 15 | |
| Thr | Ile | Lys | Leu | Asn | Ser | Asn | Lys | Lys | Tyr | Gly | Pro | Gly | Asp | Met | Thr |
| | | | 20 | | | | 25 | | | | | 30 | | | |
| Asn | Gly | Asn | Gln | Phe | Ile | Ile | Ser | Lys | Gln | Glu | Trp | Ala | Thr | Ile | Gly |
| | | 35 | | | | | 40 | | | | | 45 | | | |
| Ala | Tyr | Ile | Gln | Thr | Gly | Leu | Gly | Leu | Pro | Val | Asn | Glu | Gln | Gln | Leu |
| | 50 | | | | | 55 | | | | | 60 | | | | |
| Arg | Thr | His | Val | Asn | Leu | Ser | Gln | Asp | Ile | Ser | Ile | Pro | Ser | Asp | Phe |
| 65 | | | | | 70 | | | | | 75 | | | | | 80 |
| Ser | Gln | Leu | Tyr | Asp | Val | Tyr | Cys | Ser | Asp | Lys | Thr | Ser | Ala | Glu | Trp |
| | | | | 85 | | | | | 90 | | | | | 95 | |
| Trp | Asn | Lys | Asn | Leu | Tyr | Pro | Leu | Ile | Ile | Lys | Ser | Ala | Asn | Asp | Ile |
| | | | 100 | | | | 105 | | | | | 110 | | | |
| Ala | Ser | Tyr | Gly | Phe | Lys | Val | Ala | Gly | Asp | Pro | Ser | Ile | Lys | Lys | Asp |
| | | 115 | | | | | 120 | | | | | 125 | | | |
| Gly | Tyr | Phe | Lys | Lys | Leu | Gln | Asp | Glu | Leu | Asp | Asn | Ile | Val | Asp | Asn |
| | 130 | | | | | 135 | | | | | 140 | | | | |
| Asn | Ser | Asp | Asp | Asp | Ala | Ile | Ala | Lys | Ala | Ile | Lys | Asp | Phe | Lys | Ala |
| 145 | | | | | 150 | | | | | 155 | | | | | 160 |
| Arg | Cys | Gly | Ile | Leu | Ile | Lys | Glu | Ala | Lys | Gln | Tyr | Glu | Glu | Ala | Ala |
| | | | | 165 | | | | | 170 | | | | | 175 | |
| Lys | Asn | Ile | Val | Thr | Ser | Leu | Asp | Gln | Phe | Leu | His | Gly | Asp | Gln | Lys |
| | | | 180 | | | | 185 | | | | | 190 | | | |
| Lys | Leu | Glu | Gly | Val | Ile | Asn | Ile | Gln | Lys | Arg | Leu | Lys | Glu | Val | Gln |
| | | 195 | | | | | 200 | | | | | 205 | | | |
| Thr | Ala | Leu | Asn | Gln | Ala | His | Gly | Glu | Ser | Ser | Pro | Ala | His | Lys | Glu |
| | 210 | | | | | 215 | | | | | 220 | | | | |
| Leu | Leu | Glu | Lys | Val | Lys | Asn | Leu | Lys | Thr | Thr | Leu | Glu | Arg | Thr | Ile |
| 225 | | | | | 230 | | | | | 235 | | | | | 240 |
| Lys | Ala | Glu | Gln | Asp | Leu | Glu | Lys | Lys | Val | Glu | Tyr | Ser | Phe | Leu | Leu |
| | | | | 245 | | | | | 250 | | | | | 255 | |
| Gly | Pro | Leu | Leu | Gly | Phe | Val | Val | Tyr | Glu | Ile | Leu | Glu | Asn | Thr | Ala |
| | | | 260 | | | | 265 | | | | | 270 | | | |
| Val | Gln | His | Ile | Lys | Asn | Gln | Ile | Asp | Glu | Ile | Lys | Lys | Gln | Leu | Asp |
| | | 275 | | | | | 280 | | | | | 285 | | | |
| Ser | Ala | Gln | His | Asp | Leu | Asp | Arg | Asp | Val | Lys | Ile | Ile | Gly | Met | Leu |
| | 290 | | | | | 295 | | | | | 300 | | | | |
| Asn | Ser | Ile | Asn | Thr | Asp | Ile | Asp | Asn | Leu | Tyr | Ser | Gln | Gly | Gln | Glu |
| 305 | | | | | 310 | | | | | 315 | | | | | 320 |
| Ala | Ile | Lys | Val | Phe | Gln | Lys | Leu | Gln | Gly | Ile | Trp | Ala | Thr | Ile | Gly |
| | | | | 325 | | | | | 330 | | | | | 335 | |
| Ala | Gln | Ile | Glu | Asn | Leu | Arg | Thr | Thr | Ser | Leu | Gln | Glu | Val | Gln | Asp |
| | | | 340 | | | | 345 | | | | | 350 | | | |
| Ser | Asp | Asp | Ala | Asp | Glu | Ile | Gln | Ile | Glu | Leu | Glu | Asp | Ala | Ser | Asp |
| | | 355 | | | | | 360 | | | | | 365 | | | |
| Ala | Trp | Leu | Val | Val | Ala | Gln | Glu | Ala | Arg | Asp | Phe | Thr | Leu | Asn | Ala |
| | 370 | | | | | 375 | | | | | 380 | | | | |
| Tyr | Ser | Thr | Asn | Ser | Arg | Gln | Asn | Leu | Pro | Ile | Asn | Val | Ile | Ser | Asp |
| 385 | | | | | 390 | | | | | 395 | | | | | 400 |

-continued

| | | | | | | | | | | | | | | | |
|---|---|---|---|---|---|---|---|---|---|---|---|---|---|---|---|
| Ser | Cys | Asn | Cys | Ser 405 | Thr | Thr | Asn | Met | Thr 410 | Ser | Asn | Gln | Tyr | Ser 415 | Asn |
| Pro | Thr | Thr | Asn 420 | Met | Thr | Ser | Asn | Gln 425 | Tyr | Met | Ile | Ser | His 430 | Glu | Tyr |
| Thr | Ser | Leu 435 | Pro | Asn | Asn | Phe | Met 440 | Leu | Ser | Arg | Asn | Ser 445 | Asn | Leu | Glu |
| Tyr | Lys 450 | Cys | Pro | Glu | Asn | Asn 455 | Phe | Met | Ile | Tyr | Trp 460 | Tyr | Asn | Asn | Ser |
| Asp 465 | Trp | Tyr | Asn | Asn | Ser 470 | Asp | Trp | Tyr | Asn | Asn 475 | | | | | |

( 2 ) INFORMATION FOR SEQ ID NO:9 (PS69D1):

( i ) SEQUENCE CHARACTERISTICS:
( A ) LENGTH: 1185 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( C ) INDIVIDUAL ISOLATE: PS69D1

( v i i ) IMMEDIATE SOURCE:
( B ) CLONE: E. coli NM522(pMYC2317) NRRL B-18816

( i x ) FEATURE:
( A ) NAME/KEY: mat_peptide
( B ) LOCATION: 1..1185

( x i ) SEQUENCE DESCRIPTION: SEQ ID NO:9:

```
ATGATTTTAG GGAATGGAAA GACTTTACCA AAGCATATAA GATTAGCTCA TATTTTTGCA     60
ACACAGAATT CTTCAGCTAA GAAAGACAAT CCTCTTGGAC CAGAGGGGAT GGTTACTAAA    120
GACGGTTTTA TAATCTCTAA GGAAGAATGG GCATTTGTGC AGGCCTATGT GACTACAGGC    180
ACTGGTTTAC CTATCAATGA CGATGAGATG CGTAGACATG TTGGGTTACC ATCACGCATT    240
CAAATTCCTG ATGATTTTAA TCAATTATAT AAGGTTTATA ATGAAGATAA ACATTTATGC    300
AGTTGGTGGA ATGGTTTCTT GTTTCCATTA GTTCTTAAAA CAGCTAATGA TATTTCCGCT    360
TACGGATTTA AATGTGCTGG AAAGGGTGCC ACTAAAGGAT ATTATGAGGT CATGCAAGAC    420
GATGTAGAAA ATATTTCAGA TAATGGTTAT GATAAAGTTG CACAAGAAAA AGCACATAAG    480
GATCTGCAGG CGCGTTGTAA AATCCTTATT AAGGAGGCTG ATCAATATAA AGCTGCAGCG    540
GATGATGTTT CAAAACATTT AAACACATTT CTTAAAGGCG GTCAAGATTC AGATGGCAAT    600
GATGTTATTG GCGTAGAGGC TGTTCAAGTA CAACTAGCAC AAGTAAAAGA TAATCTTGAT    660
GGCCTATATG GCGACAAAAG CCCAAGACAT GAAGAGTTAC TAAAGAAAGT AGACGACCTG    720
AAAAAAGAGT TGGAAGCTGC TATTAAAGCA GAGAATGAAT TAGAAAAGAA AGTGAAAATG    780
AGTTTTGCTT TAGGACCATT ACTTGGATTT GTTGTATATG AAATCTTAGA GCTAACTGCG    840
GTCAAAAGTA TACACAAGAA AGTTGAGGCA CTACAAGCCG AGCTTGACAC TGCTAATGAT    900
GAACTCGACA GAGATGTAAA AATCTTAGGA ATGATGAATA GCATTGACAC TGATATTGAC    960
AACATGTTAG AGCAAGGTGA GCAAGCTCTT GTTGTATTTA GAAAAATTGC AGGCATTTGG   1020
AGTGTTATAA GTCTTAATAT CGGCAATCTT CGAGAAACAT CTTTAAAAGA GATAGAAGAA   1080
```

```
GAAAATGATG ACGATGCACT GTATATTGAG CTTGGTGATG CCGCTGGTCA ATGGAAAGAG    1140

ATAGCCGAGG AGGCACAATC CTTTGTACTA AATGCTTATA CTCCT                    1185
```

(2) INFORMATION FOR SEQ ID NO:10 (PS69D1):

(i) SEQUENCE CHARACTERISTICS:
        (A) LENGTH: 395 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: BACILLUS THURINGIENSIS
        (C) INDIVIDUAL ISOLATE: PS69D1

(vii) IMMEDIATE SOURCE:
        (B) CLONE: E. coli NM522(pMYC2317) NRRL B-18816

(ix) FEATURE:
        (A) NAME/KEY: Protein
        (B) LOCATION: 1..395

(xi) SEQUENCE DESCRIPTION: SEQ ID NO:10:

```
Met Ile Leu Gly Asn Gly Lys Thr Leu Pro Lys His Ile Arg Leu Ala
1               5                   10                  15

His Ile Phe Ala Thr Gln Asn Ser Ser Ala Lys Lys Asp Asn Pro Leu
            20                  25                  30

Gly Pro Glu Gly Met Val Thr Lys Asp Gly Phe Ile Ile Ser Lys Glu
        35                  40                  45

Glu Trp Ala Phe Val Gln Ala Tyr Val Thr Thr Gly Thr Gly Leu Pro
    50                  55                  60

Ile Asn Asp Asp Glu Met Arg Arg His Val Gly Leu Pro Ser Arg Ile
65                  70                  75                  80

Gln Ile Pro Asp Asp Phe Asn Gln Leu Tyr Lys Val Tyr Asn Glu Asp
            85                  90                  95

Lys His Leu Cys Ser Trp Trp Asn Gly Phe Leu Phe Pro Leu Val Leu
            100                 105                 110

Lys Thr Ala Asn Asp Ile Ser Ala Tyr Gly Phe Lys Cys Ala Gly Lys
        115                 120                 125

Gly Ala Thr Lys Gly Tyr Tyr Glu Val Met Gln Asp Asp Val Glu Asn
    130                 135                 140

Ile Ser Asp Asn Gly Tyr Asp Lys Val Ala Gln Glu Lys Ala His Lys
145                 150                 155                 160

Asp Leu Gln Ala Arg Cys Lys Ile Leu Ile Lys Glu Ala Asp Gln Tyr
            165                 170                 175

Lys Ala Ala Ala Asp Asp Val Ser Lys His Leu Asn Thr Phe Leu Lys
        180                 185                 190

Gly Gly Gln Asp Ser Asp Gly Asn Asp Val Ile Gly Val Glu Ala Val
    195                 200                 205

Gln Val Gln Leu Ala Gln Val Lys Asp Asn Leu Asp Gly Leu Tyr Gly
    210                 215                 220

Asp Lys Ser Pro Arg His Glu Glu Leu Leu Lys Lys Val Asp Asp Leu
225                 230                 235                 240

Lys Lys Glu Leu Glu Ala Ala Ile Lys Ala Glu Asn Glu Leu Glu Lys
            245                 250                 255
```

-continued

| | | | | | | | | | | | | | | | |
|---|---|---|---|---|---|---|---|---|---|---|---|---|---|---|---|
| Lys | Val | Lys | Met | Ser | Phe | Ala | Leu | Gly | Pro | Leu | Leu | Gly | Phe | Val | Val |
| | | | 260 | | | | | 265 | | | | | 270 | | |
| Tyr | Glu | Ile | Leu | Glu | Leu | Thr | Ala | Val | Lys | Ser | Ile | His | Lys | Lys | Val |
| | | 275 | | | | | 280 | | | | | 285 | | | |
| Glu | Ala | Leu | Gln | Ala | Glu | Leu | Asp | Thr | Ala | Asn | Asp | Glu | Leu | Asp | Arg |
| | 290 | | | | | 295 | | | | | 300 | | | | |
| Asp | Val | Lys | Ile | Leu | Gly | Met | Met | Asn | Ser | Ile | Asp | Thr | Asp | Ile | Asp |
| 305 | | | | | 310 | | | | | 315 | | | | | 320 |
| Asn | Met | Leu | Glu | Gln | Gly | Glu | Gln | Ala | Leu | Val | Val | Phe | Arg | Lys | Ile |
| | | | | 325 | | | | | 330 | | | | | 335 | |
| Ala | Gly | Ile | Trp | Ser | Val | Ile | Ser | Leu | Asn | Ile | Gly | Asn | Leu | Arg | Glu |
| | | | 340 | | | | | 345 | | | | | 350 | | |
| Thr | Ser | Leu | Lys | Glu | Ile | Glu | Glu | Glu | Asn | Asp | Asp | Asp | Ala | Leu | Tyr |
| | | 355 | | | | | 360 | | | | | 365 | | | |
| Ile | Glu | Leu | Gly | Asp | Ala | Ala | Gly | Gln | Trp | Lys | Glu | Ile | Ala | Glu | Glu |
| | 370 | | | | | 375 | | | | | 380 | | | | |
| Ala | Gln | Ser | Phe | Val | Leu | Asn | Ala | Tyr | Thr | Pro | | | | | |
| 385 | | | | | 390 | | | | | 395 | | | | | |

( 2 ) INFORMATION FOR SEQ ID NO:11:

( i ) SEQUENCE CHARACTERISTICS:
( A ) LENGTH: 2412 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Bacillus thuringiensis
( C ) INDIVIDUAL ISOLATE: PS63B ( v i i ) IMMEDIATE SOURCE:
( B ) CLONE: E. coli NM522(pMYC 1642) NRRL B-18961

( x i ) SEQUENCE DESCRIPTION: SEQ ID NO:11:

ATGACTTGTC AATTACAAGC GCAACCACTT ATTCCCTATA ACGTACTAGC AGGAGTTCCA 60
ACTAGTAATA CAGGTAGTCC AATCGGCAAT GCAGGTAATC AATTTGATCA GTTTGAGCAA 120
ACCGTTAAAG AGCTCAAGGA AGCATGGGAA GCGTTCCAAA AAAACGGAAG TTTCTCATTA 180
GCAGCTCTTG AAAAGGGATT TGATGCAGCA ATCGGAGGAG GATCCTTTGA TTATTTAGGT 240
TTAGTTCAAG CCGGCCTAGG ATTAGTTGGT ACGCTAGGCG CCGCAATCCC TGGTGTTTCA 300
GTGGCAGTGC CTCTTATTAG CATGCTTGTT GGTGTTTTTT GGCCAAAGGG CACAAACAAC 360
CAAGAAAACC TTATTACAGT TATTGATAAG GAAGTTCAGA GAATACTAGA TGAAAAGCTA 420
TCTGATCAGT TAATAAAGAA ATTGAACGCA GATTTAAATG CTTTTACGGA CCTAGTAACT 480
CGTTTGGAAG AAGTAATAAT AGATGCAACT TTCGAGAATC ACAAGCCTGT ACTACAAGTA 540
AGTAAATCAA ATTATATGAA AGTGGATTCA GCATATTTCT CAACAGGAGG TATTCTTACT 600
CTTGGCATGA GTGATTTTCT TACTGATACC TATTCAAAGC TTACCTTCCC ATTATATGTA 660
CTAGGCGCAA CTATGAAACT TTCAGCATAT CATAGTTATA TACAATTCGG AAATACATGG 720
CTTAATAAAG TTTATGATTT ATCATCAGAT GAGGGAAAAA CAATGTCGCA GGCTTTAGCA 780
CGAGCTAAAC AGCATATGCG CCAAGACATA GCATTTTATA CAAGCCAAGC TTTAAACATG 840
TTTACTGGGA ATCTCCCTTC ATTATCATCT AATAAATATG CAATTAATGA CTATAATGTA 900
TACACTCGAG CAATGGTATT GAATGGCTTA GATATAGTAG CAACATGGCC TACCCTATAT 960

-continued

```
CCAGATGACT ATTCGTCTCA GATAAAACTG GAGAAAACAC GCGTGATCTT TTCAGATATG    1020
GTCGGGCAAA GTGAGAGTAG AGATGGCAGC GTAACGATTA AAATATTTT TGACAATACA    1080
GATTCACATC AACATGGATC CATAGGTCTC AATTCAATCT CTTATTTCCC AGATGAGTTA    1140
CAGAAAGCAC AACTTCGCAT GTATGATTAT AATCACAAAC CTTATTGTAC GGACTGTTTC    1200
TGCTGGCCGT ATGGAGTGAT TTTAAACTAT AACAAGAATA CCTTTAGATA TGGCGATAAT    1260
GATCCAGGTC TTTCAGGAGA CGTTCAACTC CCAGCACCTA TGAGTGTAGT TAATGCCCAA    1320
ACTCAAACAG CCCAATATAC AGATGGAGAA AACATATGGA CAGATACTGG CCGCAGTTGG    1380
CTTTGTACTC TACGTGGCTA CTGTACTACA AACTGTTTTC CAGGAAGAGG TTGTTATAAT    1440
AATAGTACTG GATATGGAGA AAGTTGCAAT CAATCACTTC CAGGTCAAAA ATACATGCA     1500
CTATATCCTT TTACACAAAC AAATGTGCTG GGACAATCAG GCAAACTAGG ATTGCTAGCA    1560
AGTCATATTC CATATGACCT AAGTCCGAAC AATACGATTG GTGACAAAGA TACAGATTCT    1620
ACGAATATTG TCGCAAAAGG AATTCCAGTG GAAAAGGGT ATGCATCCAG TGGACAAAAA     1680
GTTGAAATTA TACGAGAGTG GATAAATGGT GCGAATGTAG TTCAATTATC TCCAGGCCAA    1740
TCTTGGGGAA TGGATTTTAC CAATAGCACA GGTGGTCAAT ATATGGTCCG CTGTCGATAT    1800
GCAAGTACAA ACGATACTCC AATCTTTTTT AATTTAGTGT ATGACGGGGG ATCGAATCCT    1860
ATTTATAACC AGATGACATT CCCTGCTACA AAAGAGACTC CAGCTCACGA TTCAGTAGAT    1920
AACAAGATAC TAGGCATAAA AGGAATAAAT GGAATTATT CACTCATGAA TGTAAAAGAT     1980
TCTGTCGAAC TTCCATCTGG GAAATTTCAT GTTTTTTCA CAAATAATGG ATCATCTGCT     2040
ATTTATTTAG ATCGACTTGA GTTTGTTCCT TTAGATCAAC CAGCAGCGCC AACACAGTCA    2100
ACACAACCAA TTAATTATCC TATCACAAGT AGGTTACCTC ATCGTTCCGG AGAACCACCT    2160
GCAATAATAT GGGAGAAATC AGGGAATGTT CGCGGGAATC AACTAACTAT ATCGGCACAA    2220
GGTGTTCCAG AAAATTCCCA AATATATCTT TCGGTGGGTG GCGATCGCCA AATTTTAGAC    2280
CGTAGCAACG GATTTAAATT AGTTAATTAC TCACCTACTT ATTCTTTCAC TAACATTCAG    2340
GCTAGCTCGT CAAATTTAGT AGATATTACA AGTGGTACCA TCACTGGCCA AGTACAAGTA    2400
TCTAATCTAT AA                                                       2412
```

(2) INFORMATION FOR SEQ ID NO:12:

(i) SEQUENCE CHARACTERISTICS:
        (A) LENGTH: 803 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (v) ORIGINAL SOURCE:
        (A) ORGANISM: Bacillus thuringiensis
        (C) INDIVIDUAL ISOLATE: PS63B

| | | | | | | | | | | | | | | |
|---|---|---|---|---|---|---|---|---|---|---|---|---|---|---|
| Asn | Gln | Phe 35 | Asp | Gln | Phe | Glu | Gln 40 | Thr | Val | Lys | Glu | Leu 45 | Lys | Glu Ala |
| Trp | Glu 50 | Ala | Phe | Gln | Lys | Asn 55 | Gly | Ser | Phe | Ser | Leu 60 | Ala | Ala | Leu Glu |
| Lys 65 | Gly | Phe | Asp | Ala | Ala 70 | Ile | Gly | Gly | Ser | Phe 75 | Asp | Tyr | Leu | Gly 80 |
| Leu | Val | Gln | Ala | Gly 85 | Leu | Gly | Leu | Val | Gly 90 | Thr | Leu | Gly | Ala | Ala Ile 95 |
| Pro | Gly | Val | Ser 100 | Val | Ala | Val | Pro | Leu 105 | Ile | Ser | Met | Leu 110 | Val | Gly Val |
| Phe | Trp | Pro 115 | Lys | Gly | Thr | Asn | Asn 120 | Gln | Glu | Asn | Leu | Ile 125 | Thr | Val Ile |
| Asp | Lys 130 | Glu | Val | Gln | Arg | Ile 135 | Leu | Asp | Glu | Lys | Leu 140 | Ser | Asp | Gln Leu |
| Ile 145 | Lys | Lys | Leu | Asn | Ala 150 | Asp | Leu | Asn | Ala | Phe 155 | Thr | Asp | Leu | Val Thr 160 |
| Arg | Leu | Glu | Glu | Val 165 | Ile | Ile | Asp | Ala | Thr 170 | Phe | Glu | Asn | His | Lys Pro 175 |
| Val | Leu | Gln | Val 180 | Ser | Lys | Ser | Asn | Tyr 185 | Met | Lys | Val | Asp | Ser 190 | Ala Tyr |
| Phe | Ser | Thr 195 | Gly | Gly | Ile | Leu | Thr 200 | Leu | Gly | Met | Ser | Asp 205 | Phe | Leu Thr |
| Asp | Thr 210 | Tyr | Ser | Lys | Leu | Thr 215 | Phe | Pro | Leu | Tyr | Val 220 | Leu | Gly | Ala Thr |
| Met 225 | Lys | Leu | Ser | Ala | Tyr 230 | His | Ser | Tyr | Ile | Gln 235 | Phe | Gly | Asn | Thr Trp 240 |
| Leu | Asn | Lys | Val | Tyr 245 | Asp | Leu | Ser | Ser | Asp 250 | Glu | Gly | Lys | Thr | Met Ser 255 |
| Gln | Ala | Leu | Ala | Arg 260 | Ala | Lys | Gln | His | Met 265 | Arg | Gln | Asp | Ile 270 | Ala Phe |
| Tyr | Thr | Ser 275 | Gln | Ala | Leu | Asn | Met 280 | Phe | Thr | Gly | Asn | Leu 285 | Pro | Ser Leu |
| Ser | Ser 290 | Asn | Lys | Tyr | Ala | Ile 295 | Asn | Asp | Tyr | Asn | Val 300 | Tyr | Thr | Arg Ala |
| Met 305 | Val | Leu | Asn | Gly | Leu 310 | Asp | Ile | Val | Ala | Thr 315 | Trp | Pro | Thr | Leu Tyr 320 |
| Pro | Asp | Asp | Tyr | Ser 325 | Ser | Gln | Ile | Lys | Leu 330 | Glu | Lys | Thr | Arg | Val Ile 335 |
| Phe | Ser | Asp | Met 340 | Val | Gly | Gln | Ser | Glu 345 | Ser | Arg | Asp | Gly | Ser 350 | Val Thr |
| Ile | Lys | Asn 355 | Ile | Phe | Asp | Asn | Thr 360 | Asp | Ser | His | Gln | His 365 | Gly | Ser Ile |
| Gly | Leu 370 | Asn | Ser | Ile | Ser | Tyr 375 | Phe | Pro | Asp | Glu | Leu 380 | Gln | Lys | Ala Gln |
| Leu 385 | Arg | Met | Tyr | Asp | Tyr 390 | Asn | His | Lys | Pro | Tyr 395 | Cys | Thr | Asp | Cys Phe 400 |
| Cys | Trp | Pro | Tyr | Gly 405 | Val | Ile | Leu | Asn | Tyr 410 | Asn | Lys | Asn | Thr | Phe Arg 415 |
| Tyr | Gly | Asp | Asn 420 | Asp | Pro | Gly | Leu | Ser 425 | Gly | Asp | Val | Gln | Leu 430 | Pro Ala |
| Pro | Met | Ser 435 | Val | Val | Asn | Ala | Gln 440 | Thr | Gln | Thr | Ala | Gln 445 | Tyr | Thr Asp |
| Gly | Glu | Asn | Ile | Trp | Thr | Asp | Thr | Gly | Arg | Ser | Trp | Leu | Cys | Thr Leu |

|     |     |     |     |     |     |     |     |     |     |     |     |     |     |     |
| --- | --- | --- | --- | --- | --- | --- | --- | --- | --- | --- | --- | --- | --- | --- |
| | | | | 450 | | | | | 455 | | | | | 460 |
| Arg 465 | Gly | Tyr | Cys | Thr | Thr 470 | Asn | Cys | Phe | Pro | Gly 475 | Arg | Gly | Cys | Tyr | Asn 480 |
| Asn | Ser | Thr | Gly | Tyr 485 | Gly | Glu | Ser | Cys | Asn 490 | Gln | Ser | Leu | Pro | Gly 495 | Gln |
| Lys | Ile | His | Ala 500 | Leu | Tyr | Pro | Phe | Thr 505 | Gln | Thr | Asn | Val | Leu 510 | Gly | Gln |
| Ser | Gly | Lys 515 | Leu | Gly | Leu | Leu | Ala 520 | Ser | His | Ile | Pro | Tyr 525 | Asp | Leu | Ser |
| Pro | Asn 530 | Asn | Thr | Ile | Gly | Asp 535 | Lys | Asp | Thr | Asp | Ser 540 | Thr | Asn | Ile | Val |
| Ala 545 | Lys | Gly | Ile | Pro | Val 550 | Glu | Lys | Gly | Tyr | Ala 555 | Ser | Ser | Gly | Gln | Lys 560 |
| Val | Glu | Ile | Ile | Arg 565 | Glu | Trp | Ile | Asn | Gly 570 | Ala | Asn | Val | Val | Gln 575 | Leu |
| Ser | Pro | Gly | Gln 580 | Ser | Trp | Gly | Met | Asp 585 | Phe | Thr | Asn | Ser | Thr 590 | Gly | Gly |
| Gln | Tyr | Met 595 | Val | Arg | Cys | Arg | Tyr 600 | Ala | Ser | Thr | Asn | Asp 605 | Thr | Pro | Ile |
| Phe | Phe 610 | Asn | Leu | Val | Tyr | Asp 615 | Gly | Gly | Ser | Asn | Pro 620 | Ile | Tyr | Asn | Gln |
| Met 625 | Thr | Phe | Pro | Ala | Thr 630 | Lys | Glu | Thr | Pro | Ala 635 | His | Asp | Ser | Val | Asp 640 |
| Asn | Lys | Ile | Leu | Gly 645 | Ile | Lys | Gly | Ile | Asn 650 | Gly | Asn | Tyr | Ser | Leu 655 | Met |
| Asn | Val | Lys | Asp 660 | Ser | Val | Glu | Leu | Pro 665 | Ser | Gly | Lys | Phe | His 670 | Val | Phe |
| Phe | Thr | Asn 675 | Asn | Gly | Ser | Ser | Ala 680 | Ile | Tyr | Leu | Asp | Arg 685 | Leu | Glu | Phe |
| Val | Pro 690 | Leu | Asp | Gln | Pro | Ala 695 | Ala | Pro | Thr | Gln | Ser 700 | Thr | Gln | Pro | Ile |
| Asn 705 | Tyr | Pro | Ile | Thr | Ser 710 | Arg | Leu | Pro | His | Arg 715 | Ser | Gly | Glu | Pro | Pro 720 |
| Ala | Ile | Ile | Trp | Glu 725 | Lys | Ser | Gly | Asn | Val 730 | Arg | Gly | Asn | Gln | Leu 735 | Thr |
| Ile | Ser | Ala | Gln 740 | Gly | Val | Pro | Glu | Asn 745 | Ser | Gln | Ile | Tyr | Leu 750 | Ser | Val |
| Gly | Gly | Asp 755 | Arg | Gln | Ile | Leu | Asp 760 | Arg | Ser | Asn | Gly | Phe 765 | Lys | Leu | Val |
| Asn | Tyr 770 | Ser | Pro | Thr | Tyr | Ser 775 | Phe | Thr | Asn | Ile | Gln 780 | Ala | Ser | Ser | Ser |
| Asn 785 | Leu | Val | Asp | Ile | Thr 790 | Ser | Gly | Thr | Ile | Thr 795 | Gly | Gln | Val | Gln | Val 800 |
| Ser | Asn | Leu | | | | | | | | | | | | | |

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
    Arg Glu Trp Ile Asn Gly Ala Asn
    1               5
```

( 2 ) INFORMATION FOR SEQ ID NO:14:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:14:

```
AGARTRKWTW AATGGWGCKM AW                                          22
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
    Pro Thr Phe Asp Pro Asp Leu Tyr
    1               5
```

( 2 ) INFORMATION FOR SEQ ID NO:16:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:16:

```
CCNACYTTTK ATCCAGATSW YTAT                                        24
```

( 2 ) INFORMATION FOR SEQ ID NO:17:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

```
    Ala Ile Leu Asn Glu Leu Tyr Pro Ser Val Pro Tyr Asn Val
    1               5                   10
```

( 2 ) INFORMATION FOR SEQ ID NO:18:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
    Ala Ile Leu Asn Glu Leu Tyr Pro Ser Val Pro Tyr Asn Val
    1               5                   10
```

( 2 ) INFORMATION FOR SEQ ID NO:19:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
Met Ile Ile Asp Ser Lys Thr Thr Leu Pro Arg His Ser Leu Ile Asn
1               5                   10                  15
Thr
```

( 2 ) INFORMATION FOR SEQ ID NO:20:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

```
Gln Leu Gln Ala Gln Pro Leu Ile Pro Tyr Asn Val Leu Ala
1               5                   10
```

( 2 ) INFORMATION FOR SEQ ID NO:21:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Met Ile Leu Gly Asn Gly Lys Thr Leu Pro Lys His Ile Arg Leu Ala
1               5                   10                  15
His Ile Phe Ala Thr Gln Asn Ser
                20
```

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

```
Ala Thr Leu Asn Glu Val Tyr Pro Val Asn
1               5                   10
```

( 2 ) INFORMATION FOR SEQ ID NO:23:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

Val Gln Arg Ile Leu Asp Glu Lys Leu Ser Phe Gln Leu Ile Lys
1               5                   10                  15

( 2 ) INFORMATION FOR SEQ ID NO:24:

( i ) SEQUENCE CHARACTERISTICS:
    ( A ) LENGTH: 23 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:24:

GCAATTTTAA ATGAATTATA TCC                                                    23

( 2 ) INFORMATION FOR SEQ ID NO:25:

( i ) SEQUENCE CHARACTERISTICS:
    ( A ) LENGTH: 56 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:25:

ATGATTATTG ATTCTAAAAC AACATTACCA AGACATTCWT TAATWAATAC WATWAA              56

( 2 ) INFORMATION FOR SEQ ID NO:26:

( i ) SEQUENCE CHARACTERISTICS:
    ( A ) LENGTH: 38 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:26:

AAACATATTA GATTAGCACA TATTTTGCA ACACAAAA                                    38

( 2 ) INFORMATION FOR SEQ ID NO:27:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:27:

CAAYTACAAG CWCAACC                                                           17

( 2 ) INFORMATION FOR SEQ ID NO:28:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:28:

TTCATCTAAA ATTCTTTGWA C                                                      21

( 2 ) INFORMATION FOR SEQ ID NO:29:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:29:

```
Leu Asp Arg Ile Gln Phe Ile Pro
 1               5
```

( 2 ) INFORMATION FOR SEQ ID NO:30:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:30:

AGGAACAAAY TCAAKWCGRT CTA                                                2 3

( 2 ) INFORMATION FOR SEQ ID NO:31:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:31:

```
Tyr Ile Asp Lys Ile Glu Phe Ile Pro
 1               5
```

( 2 ) INFORMATION FOR SEQ ID NO:32:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:32:

TGGAATAAAT TCAATTYKRT CWA                                                2 3

( 2 ) INFORMATION FOR SEQ ID NO:33:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:33:

GCWACWTTAA ATGAAGTWTA T                                                  2 1

( 2 ) INFORMATION FOR SEQ ID NO:34:

( i ) SEQUENCE CHARACTERISTICS:
  ( A ) LENGTH: 21 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:34:

AATGAAGTWT ATCCWGTWAA T                                             21

( 2 ) INFORMATION FOR SEQ ID NO:35:

( i ) SEQUENCE CHARACTERISTICS:
    ( A ) LENGTH: 38 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:35:

GCAAGCGGCC GCTTATGGAA TAAATTCAAT TYKRTCWA                            38

( 2 ) INFORMATION FOR SEQ ID NO:36:

( i ) SEQUENCE CHARACTERISTICS:
    ( A ) LENGTH: 28 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:36:

TGATTTTWMT CAATTATATR AKGTTTAT                                      28

( 2 ) INFORMATION FOR SEQ ID NO:37:

( i ) SEQUENCE CHARACTERISTICS:
    ( A ) LENGTH: 20 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:37:

AAGAGTTAYT ARARAAAGTA                                               20

( 2 ) INFORMATION FOR SEQ ID NO:38:

( i ) SEQUENCE CHARACTERISTICS:
    ( A ) LENGTH: 35 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:38:

TTAGGACCAT TRYTWGGATT TGTTGTWTAT GAAAT                              35

( 2 ) INFORMATION FOR SEQ ID NO:39:

( i ) SEQUENCE CHARACTERISTICS:
    ( A ) LENGTH: 27 bases
    ( B ) TYPE: nucleic acid
    ( C ) STRANDEDNESS: single (D) TOPOLOGY: linear (ii) MOLECULE TYPE: DNA (synthetic)

(xi) SEQUENCE DESCRIPTION: SEQ ID NO:39:

GAYAGAGATG TWAAAATYWT AGGAATG  27

(2) INFORMATION FOR SEQ ID NO:40:

(i) SEQUENCE CHARACTERISTICS:
(A) LENGTH: 23 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:40:

TTMTTAAAWC WGCTAATGAT ATT  23

(2) INFORMATION FOR SEQ ID NO:41:

(i) SEQUENCE CHARACTERISTICS:
(A) LENGTH: 716 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:41:

| Met | Xaa | Xaa | Xaa | Xaa | Xaa | Xaa | Xaa | Pro | Xaa | Xaa | Pro | Tyr | Asn | Xaa | Xaa |
|---|---|---|---|---|---|---|---|---|---|---|---|---|---|---|---|
| 1 | | | | 5 | | | | | 10 | | | | | | 15 |
| Xaa | Xaa | Xaa | Pro | Xaa | Xaa | Xaa | Xaa | Xaa | Xaa | Xaa | Xaa | Xaa | Xaa | Xaa | Xaa |
| | | | 20 | | | | | 25 | | | | | 30 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 35 | | | | | 40 | | | | | 45 | | |
| Xaa | Xaa | Xaa | Xaa | Xaa | Xaa | Xaa | Xaa | Xaa | Xaa | Xaa | Xaa | Xaa | Xaa | Xaa | Xaa |
| | 50 | | | | | 55 | | | | | 60 | | | | |
| Xaa | Xaa | Xaa | Xaa | Xaa | Xaa | Xaa | Xaa | Xaa | Xaa | Xaa | Xaa | Xaa | Xaa | Tyr | Xaa |
| 65 | | | | | 70 | | | | | 75 | | | | | 80 |
| Xaa | Xaa | Val | Xaa | Xaa | Xaa | Xaa | Xaa | Xaa | Xaa | Xaa | Xaa | Xaa | Xaa | Xaa | Xaa |
| | | | | 85 | | | | | 90 | | | | | 95 | |
| Xaa | Pro | Xaa | Xaa | Xaa | Xaa | Xaa | Xaa | Pro | Xaa | Xaa | Xaa | Xaa | Xaa | Xaa | Xaa |
| | | | 100 | | | | | 105 | | | | | 110 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 115 | | | | | 120 | | | | | 125 | | |
| Xaa | Xaa | Xaa | Xaa | Xaa | Xaa | Xaa | Xaa | Xaa | Xaa | Xaa | Asp | Xaa | Xaa | Xaa | |
| | 130 | | | | | 135 | | | | | 140 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 145 | | | | | 150 | | | | | 155 | | | | | 160 |
| Xaa | Xaa | Xaa | Xaa | Xaa | Xaa | Xaa | Xaa | Xaa | Xaa | Xaa | Xaa | Xaa | Xaa | Xaa | Xaa |
| | | | | 165 | | | | | 170 | | | | | 175 | |
| Xaa | His | Xaa | Xaa | Xaa | Xaa | Xaa | Xaa | Xaa | Xaa | Xaa | Xaa | Xaa | Xaa | Xaa | Xaa |
| | | | 180 | | | | | 185 | | | | | 190 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 195 | | | | | 200 | | | | | 205 | | |
| Xaa | Xaa | Xaa | Xaa | Xaa | Xaa | Xaa | Xaa | Xaa | Xaa | Xaa | Leu | Xaa | Xaa | Pro | |
| | 210 | | | | | 215 | | | | | 220 | | | | |
| Xaa | Tyr | Xaa | Xaa | Xaa | Xaa | Xaa | Met | Xaa | Xaa | Xaa | Xaa | Xaa | Xaa | Xaa | Xaa |
| 225 | | | | | 230 | | | | | 235 | | | | | 240 |

```
Xaa Xaa Xaa Xaa Xaa Xaa Trp Xaa Xaa Xaa Xaa Xaa Xaa Xaa Xaa
            245                 250                 255
Xaa Xaa Xaa Xaa Xaa Xaa Xaa Xaa Xaa Xaa Xaa Xaa Xaa Xaa Xaa
            260                 265                 270
Xaa Xaa Xaa Xaa Xaa Xaa Tyr Xaa Xaa Xaa Xaa Xaa Xaa Xaa Xaa
            275                 280                 285
Xaa Xaa Xaa Xaa Xaa Xaa Xaa Xaa Xaa Xaa Xaa Xaa Xaa Xaa Xaa
            290                 295                 300
Xaa Xaa Xaa Xaa Xaa Tyr Xaa Xaa Xaa Met Xaa Xaa Xaa Xaa Xaa
305                 310                 315                 320
Xaa Xaa Xaa Xaa Xaa Pro Xaa Xaa Xaa Pro Xaa Xaa Tyr Xaa Xaa
            325                 330                 335
Xaa Xaa Xaa Xaa Xaa Xaa Xaa Xaa Xaa Xaa Xaa Xaa Xaa Xaa Xaa
            340                 345                 350
Xaa Xaa Xaa Xaa Xaa Xaa Xaa Xaa Xaa Xaa Xaa Xaa Xaa Xaa Xaa
            355                 360                 365
Xaa Xaa Xaa Xaa Xaa Xaa Xaa Xaa Xaa Xaa Xaa Xaa Xaa Xaa Xaa
            370                 375                 380
Xaa Xaa Xaa Xaa Xaa Xaa Xaa Xaa Xaa Xaa Xaa Xaa Xaa Xaa Tyr
385                 390                 395                 400
Xaa Xaa Xaa Xaa Xaa Xaa Xaa Xaa Xaa Xaa Xaa Xaa Xaa Tyr Xaa
            405                 410                 415
Xaa Xaa Xaa Xaa Xaa Xaa Xaa Xaa Xaa Xaa Xaa Xaa Tyr Xaa Xaa
            420                 425                 430
Xaa Xaa Xaa Xaa Xaa Pro Xaa Xaa Xaa Xaa Xaa Xaa Xaa Xaa Xaa
            435                 440                 445
Xaa Xaa Xaa Pro Xaa Xaa Xaa Xaa Xaa Xaa Xaa Xaa Xaa Xaa Xaa
            450                 455                 460
Xaa Xaa Xaa Xaa Xaa Xaa Xaa Xaa Xaa Xaa Xaa Xaa Xaa Xaa Xaa
465                 470                 475                 480
Xaa Xaa Xaa Xaa Xaa Xaa Xaa Xaa Xaa Xaa Xaa Xaa Xaa Xaa Xaa
            485                 490                 495
Xaa Xaa Xaa Xaa Xaa Xaa Xaa Xaa Xaa Xaa Xaa Xaa Xaa Xaa Xaa
            500                 505                 510
Xaa Xaa Xaa Xaa Xaa Xaa Xaa Xaa Xaa Xaa Xaa Xaa Xaa Xaa Xaa
            515                 520                 525
Xaa Xaa Xaa Xaa Xaa Xaa Xaa Xaa Xaa Xaa Xaa Xaa Xaa Xaa Xaa
            530                 535                 540
Xaa Xaa Xaa Pro Xaa Xaa Xaa Xaa Xaa Xaa Xaa Xaa Xaa Xaa Xaa
545                 550                 555                 560
Xaa Xaa Xaa Xaa Xaa Xaa Xaa Xaa Xaa Xaa Xaa Pro Xaa Xaa Xaa
            565                 570                 575
Xaa Xaa Xaa Xaa Xaa Xaa Xaa Xaa Xaa Xaa Xaa Xaa Xaa Trp Leu
            580                 585                 590
Xaa Xaa Xaa Xaa Xaa Xaa Xaa Xaa Xaa Pro Xaa Xaa Xaa Xaa Xaa
            595                 600                 605
Xaa Xaa Xaa Xaa Xaa Xaa Xaa Xaa Xaa Tyr Xaa Xaa Arg Cys Arg Tyr
            610                 615                 620
Xaa Xaa Xaa Xaa Xaa Xaa Xaa Xaa Xaa Xaa Xaa Xaa Xaa Xaa Xaa
625                 630                 635                 640
Xaa Xaa Xaa Pro Xaa Xaa Xaa Xaa Xaa Xaa Xaa Xaa Xaa Xaa Xaa
            645                 650                 655
Xaa Xaa Xaa Xaa Xaa Xaa Xaa Xaa Xaa Xaa Xaa Xaa Xaa Xaa Xaa
```

|     |     |     |     |     | 660 |     |     |     | 665 |     |     |     |     | 670 |
| --- | --- | --- | --- | --- | --- | --- | --- | --- | --- | --- | --- | --- | --- | --- |
| Xaa | Xaa | Xaa | Xaa | Xaa | Xaa | Xaa | Xaa | Xaa | Xaa | Xaa | Xaa | Xaa | Xaa | Xaa |
|     |     | 675 |     |     |     |     | 680 |     |     |     |     | 685 |     |     |
| Pro | Xaa | Xaa | Xaa | Xaa | Xaa | Xaa | Xaa | Xaa | Xaa | Xaa | Xaa | Xaa | Ser | Ser | Xaa |
|     |     | 690 |     |     |     |     | 695 |     |     |     |     | 700 |     |     |
| Xaa | Xaa | Xaa | Asp | Xaa | Xaa | Glu | Xaa | Xaa | Pro | Xaa | Xaa |
| 705 |     |     |     |     | 710 |     |     |     |     | 715 |     |

( 2 ) INFORMATION FOR SEQ ID NO:42:

( i ) SEQUENCE CHARACTERISTICS:
    ( A ) LENGTH: 401 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Duplication
    ( B ) LOCATION: 400..401
    ( D ) OTHER INFORMATION: /note= "This sequence can be from
      401-500 amino acids in length. The last 100 amino acids
      can be any amino acid in accordance with the Generic
      Formula II."

( x i ) SEQUENCE DESCRIPTION: SEQ ID NO:42:

| Met | Xaa | Xaa | Xaa | Xaa | Xaa | Xaa | Xaa | Xaa | Pro | Lys | His | Xaa | Xaa | Xaa | Xaa |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Xaa | Xaa | Xaa | Xaa | Xaa | Xaa | Xaa | Xaa | Xaa | Xaa | Xaa | Xaa | Xaa | Xaa | Xaa |
|     |     |     | 20 |     |     |     |     | 25 |     |     |     |     | 30 |     |
| Xaa | Pro | Xaa | Xaa | Xaa | Xaa | Xaa | Xaa | Xaa | Xaa | Xaa | Xaa | Xaa | Xaa | Xaa |
|     |     |     | 35 |     |     |     |     | 40 |     |     |     |     | 45 |     |
| Xaa | Trp | Xaa | Xaa | Xaa | Xaa | Xaa | Tyr | Xaa | Xaa | Xaa | Xaa | Xaa | Xaa | Xaa | Pro |
|     |     | 50 |     |     |     |     | 55 |     |     |     |     | 60 |     |     |
| Xaa | Xaa | Xaa | Xaa | Xaa | Xaa | Xaa | Xaa | His | Xaa | Xaa | Xaa | Xaa | Xaa | Xaa | Xaa |
| 65 |     |     |     |     | 70 |     |     |     |     | 75 |     |     |     |     | 80 |
| Xaa | Xaa | Pro | Xaa | Xaa | Xaa | Xaa | Xaa | Xaa | Tyr | Xaa | Xaa | Tyr | Xaa | Xaa | Xaa |
|     |     |     |     | 85 |     |     |     |     | 90 |     |     |     |     | 95 |     |
| Xaa | Xaa | Xaa | Xaa | Xaa | Trp | Trp | Xaa | Xaa | Xaa | Xaa | Xaa | Pro | Xaa | Xaa | Xaa |
|     |     |     |     | 100 |     |     |     |     | 105 |     |     |     |     | 110 |     |
| Xaa | Xaa | Xaa | Xaa | Xaa | Xaa | Xaa | Xaa | Tyr | Xaa | Xaa | Xaa | Xaa | Xaa | Xaa | Xaa |
|     |     |     | 115 |     |     |     |     | 120 |     |     |     |     | 125 |     |     |
| Xaa | Xaa | Lys | Xaa | Xaa | Xaa | Xaa | Xaa | Xaa | Xaa | Xaa | Xaa | Xaa | Xaa | Xaa | Xaa |
|     |     | 130 |     |     |     |     | 135 |     |     |     |     | 140 |     |     |
| Xaa | Xaa | Xaa | Xaa | Xaa | Xaa | Xaa | Xaa | Xaa | Xaa | Xaa | Xaa | Xaa | Xaa | Xaa | Xaa |
| 145 |     |     |     |     | 150 |     |     |     |     | 155 |     |     |     |     | 160 |
| Xaa | Xaa | Xaa | Xaa | Xaa | Xaa | Xaa | Cys | Xaa | Xaa | Xaa | Xaa | Lys | Glu | Xaa | Xaa |
|     |     |     |     | 165 |     |     |     |     | 170 |     |     |     |     | 175 |     |
| Xaa | Tyr | Xaa | Xaa | Xaa | Xaa | Xaa | Xaa | Xaa | Xaa | Xaa | Xaa | Xaa | Xaa | Xaa | Xaa |
|     |     |     | 180 |     |     |     |     | 185 |     |     |     |     | 190 |     |     |
| Xaa | Xaa | Xaa | Xaa | Xaa | Xaa | Xaa | Xaa | Xaa | Xaa | Xaa | Xaa | Xaa | Xaa | Xaa |
|     |     |     | 195 |     |     |     |     | 200 |     |     |     |     | 205 |     |
| Xaa | Xaa | Xaa | Xaa | Xaa | Xaa | Xaa | Xaa | Xaa | Xaa | Xaa | Xaa | Xaa | Xaa | Xaa |
|     |     | 210 |     |     |     |     | 215 |     |     |     |     | 220 |     |     |
| Xaa | Xaa | Xaa | Xaa | Xaa | Pro | Xaa | Xaa | Xaa | Xaa | Xaa | Xaa | Xaa | Xaa | Xaa | Xaa |
| 225 |     |     |     |     | 230 |     |     |     |     | 235 |     |     |     |     | 240 |
| Xaa | Xaa | Xaa | Xaa | Xaa | Leu | Glu | Xaa | Xaa | Xaa | Xaa | Xaa | Xaa | Xaa | Xaa |
|     |     |     |     | 245 |     |     |     |     | 250 |     |     |     |     | 255 |

| Xaa | Lys | Lys | Xaa 260 | Xaa | Xaa | Xaa | Xaa | Xaa 265 | Xaa | Xaa | Pro | Xaa | Xaa 270 | Xaa | Xaa |
|---|---|---|---|---|---|---|---|---|---|---|---|---|---|---|---|
| Xaa | Xaa | Tyr 275 | Xaa | Xaa | Xaa | Xaa | Xaa 280 | Xaa | Xaa | Xaa | Xaa | Xaa 285 | Xaa | Xaa | Xaa |
| Xaa | Xaa 290 | Xaa | Xaa | Xaa | Xaa | Xaa 295 | Xaa | Xaa | Xaa | Xaa | Xaa 300 | Xaa | Xaa | Xaa | Xaa |
| Xaa 305 | Xaa | Xaa | Xaa | Xaa | Xaa 310 | Xaa | Xaa | Xaa | Xaa | Xaa 315 | Xaa | Xaa | Xaa | Xaa | Xaa 320 |
| Xaa | Xaa | Xaa | Xaa | Xaa 325 | Xaa | Xaa | Xaa | Xaa | Xaa 330 | Xaa | Xaa | Xaa | Xaa | Xaa 335 | Xaa |
| Xaa | Xaa | Xaa | Xaa 340 | Xaa | Trp | Xaa | Xaa | Xaa 345 | Xaa | Xaa | Xaa | Xaa | Xaa 350 | Xaa | Xaa |
| Xaa | Xaa | Xaa 355 | Xaa | Xaa | Xaa | Xaa | Xaa 360 | Xaa | Xaa | Xaa | Xaa | Xaa 365 | Xaa | Xaa | Xaa |
| Xaa | Xaa 370 | Xaa | Xaa | Xaa | Xaa | Xaa 375 | Xaa | Xaa | Xaa | Xaa | Trp 380 | Xaa | Xaa | Xaa | Xaa |
| Xaa 385 | Xaa | Xaa | Xaa | Xaa | Xaa 390 | Xaa | Xaa | Xaa | Xaa | Tyr 395 | Xaa | Xaa | Xaa | Xaa | Xaa 400 |
| Xaa | | | | | | | | | | | | | | | |